(12) United States Patent
Vassilev

(10) Patent No.: US 11,285,205 B2
(45) Date of Patent: Mar. 29, 2022

(54) INFLUENZA ANTIGENS

(71) Applicant: GLAXOSMITHKLINE BIOLOGICALS S.A., Rixensart (BE)

(72) Inventor: Ventzislav Bojidarov Vassilev, Rixensart (BE)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 183 days.

(21) Appl. No.: 16/078,196

(22) PCT Filed: Mar. 2, 2017

(86) PCT No.: PCT/EP2017/054843
§ 371 (c)(1),
(2) Date: Aug. 21, 2018

(87) PCT Pub. No.: WO2017/149054
PCT Pub. Date: Sep. 8, 2017

(65) Prior Publication Data
US 2019/0054163 A1    Feb. 21, 2019

(30) Foreign Application Priority Data
Mar. 2, 2016  (GB) ..................... 1603625

(51) Int. Cl.
*A61K 39/145* (2006.01)
*C07K 14/005* (2006.01)
*A61K 39/12* (2006.01)
*A61P 31/16* (2006.01)
*C12N 15/62* (2006.01)
*A61K 39/00* (2006.01)

(52) U.S. Cl.
CPC ............ *A61K 39/145* (2013.01); *A61K 39/12* (2013.01); *A61P 31/16* (2018.01); *C07K 14/005* (2013.01); *C12N 15/62* (2013.01); *A61K 2039/55511* (2013.01); *A61K 2039/55577* (2013.01); *C12N 2760/16134* (2013.01)

(58) Field of Classification Search
None
See application file for complete search history.

(56) References Cited

U.S. PATENT DOCUMENTS

2008/0032921 A1* 2/2008 Alexander .............. A61P 43/00
424/526

OTHER PUBLICATIONS

Langley et al., Immunogenicity of heterologous H5N1 influenza booster vaccination6 or 18 months after primary vaccination in adults: A randomizedcontrolled clinical trial, 2015, Vaccine, vol. 33, pp. 559-567.*
Cross et al., Composition and functions of the influenza fusion peptide, 2009, Protein Peptide Letters, vol. 16, No. 7, pp. 766-778, abstract provided.*
Florian Krammer, et al. "A Carboxy-Terminal Trimerization Domain Stabilizes Conformational Epitopes on the Stalk Domain of Soluble Recombinant Hemagglutinin Substrates". PLOS One, 7(8): e43603 (Aug. 23, 2012). XP055181050.
Shujuan Cui, et al. "Secretory Expression of all 16 Subtypes of the Hemagglutinin 1 Protein of Influenza A Virus in Insect Cells". Journal of Virological Methods, 177(2): 160-167 (Jul. 25, 2011). XP028297787.
R. Hai, et al. "Influenza Viruses Expressing Chimeric Hemagglutinins: Globular Head and Stalk Domains Derived from Different Subtypes". Journal of Virology, 86(10): 5774-5781 (Mar. 7, 2012).
Armstrong et al., The Journal of Cell Biology, 151(2): 425-437 (2000).

* cited by examiner

*Primary Examiner* — Benjamin P Blumel

(57) ABSTRACT

The present invention relates to novel influenza antigens, novel immunogenic or vaccine compositions, as well as to uses of and to methods for producing said antigens and compositions. In particular, the invention relates to recombinant forms of hemagglutinin (HA) and their use in vaccine compositions for the prevention of influenza virus infections.

26 Claims, 9 Drawing Sheets
Specification includes a Sequence Listing.

Figure 2

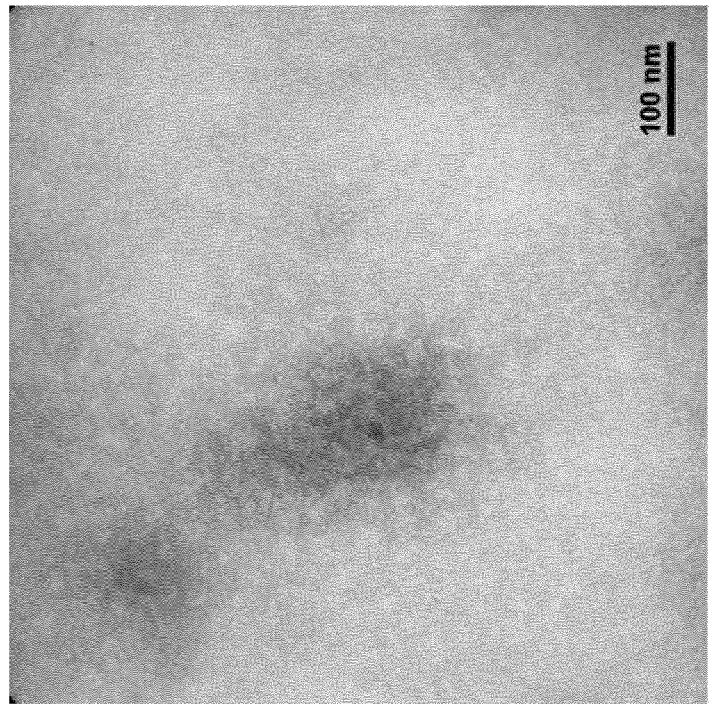
Figure 3B ECD-TMD-FOLDON
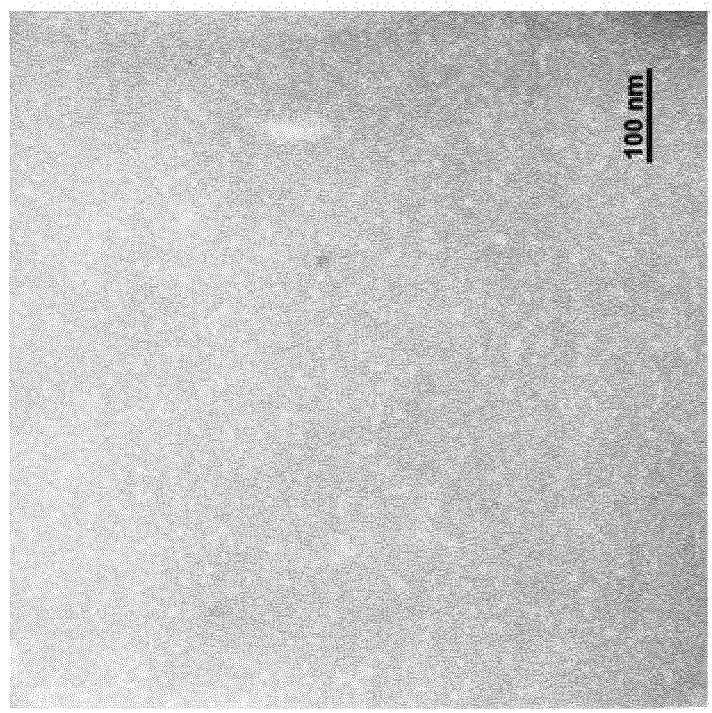
Figure 3A ECD-FOLDON

SEQUENCE LISTING

<160> NUMBER OF SEQ ID NOS: 11

<210> SEQ ID NO 1
<211> LENGTH: 588
<212> TYPE: PRT
<213> ORGANISM: Artificial Sequence
<220> FEATURE:
<223> OTHER INFORMATION: Recombinant H5 haemagglutinin (ECD-TMD-foldon) Indo05

<400> SEQUENCE: 1

```
Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Thr His Asn Gly Lys Leu Cys Asp Leu Asp Gly Val Lys
        35                  40                  45

Pro Leu Ile Leu Arg Asp Cys Ser Val Ala Gly Trp Leu Leu Gly Asn
50                  55                  60

Pro Met Cys Asp Glu Phe Ile Asn Val Pro Glu Trp Ser Tyr Ile Val
65                  70                  75                  80

Glu Lys Ala Asn Pro Thr Asn Asp Leu Cys Tyr Pro Gly Ser Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Ser Asp His Glu Ala Ser
        115                 120                 125

Ser Gly Asx Ser Ser Ala Cys Pro Tyr Leu Gly Ser Pro Ser Phe Phe
    130                 135                 140

Arg Asn Val Val Trp Leu Ile Lys Lys Asn Ser Thr Tyr Pro Thr Ile
145                 150                 155                 160

Lys Lys Ser Tyr Asn Asn Thr Asn Gln Glu Asp Leu Leu Val Leu Trp
                165                 170                 175

Gly Ile His His Pro Asn Asp Ala Ala Glu Gln Thr Arg Leu Tyr Gln
            180                 185                 190

Asn Pro Thr Thr Tyr Ile Ser Ile Gly Thr Ser Thr Leu Asn Gln Arg
        195                 200                 205

Leu Val Pro Lys Ile Ala Thr Arg Ser Lys Val Asn Gly Gln Ser Gly
    210                 215                 220

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Ala Ile Met Lys Ser Glu Leu Glu Tyr Gly
```

```
            260                 265                 270
Asn Cys Asn Thr Lys Cys Gln Thr Pro Met Gly Ala Ile Asn Ser Ser
            275                 280                 285
Pro Met Phe His Asn Ile His Pro Leu Thr Ile Gly Glu Cys Pro Lys
            290                 295                 300
Tyr Asx Lys Ser Asn Arg Leu Val Leu Ala Thr Gly Leu Arg Asn Ser
305                 310                 315                 320
Pro Gln Arg Glu Ser Arg Arg Lys Lys Arg Gly Leu Phe Gly Ala Ile
                325                 330                 335
Ala Gly Phe Ile Glu Gly Gly Trp Gln Gly Met Val Asp Gly Trp Tyr
                340                 345                 350
Gly Tyr His His Ser Asn Glu Gln Gly Ser Gly Tyr Ala Ala Asp Lys
                355                 360                 365
Glu Ser Thr Gln Lys Ala Ile Asp Gly Val Thr Asn Lys Val Asn Ser
            370                 375                 380
Ile Ile Asp Lys Met Asn Thr Gln Phe Glu Ala Val Gly Arg Glu Phe
385                 390                 395                 400
Asn Asn Leu Glu Arg Arg Ile Glu Asn Leu Asn Lys Lys Met Glu Asp
                405                 410                 415
Gly Phe Leu Asp Val Trp Thr Tyr Asn Ala Glu Leu Leu Val Leu Met
                420                 425                 430
Glu Asn Glu Arg Thr Leu Asp Phe His Asp Ser Asn Val Lys Asn Leu
            435                 440                 445
Tyr Asp Lys Val Arg Leu Gln Leu Arg Asp Asn Ala Lys Glu Leu Gly
450                 455                 460
Asn Gly Cys Phe Glu Phe Tyr His Lys Cys Asp Asn Glu Cys Met Glu
465                 470                 475                 480
Ser Ile Arg Asn Gly Thr Tyr Asn Tyr Pro Gln Tyr Ser Glu Glu Ala
                485                 490                 495
Arg Leu Lys Arg Glu Glu Ile Ser Gly Val Lys Leu Glu Ser Ile Gly
                500                 505                 510
Thr Tyr Gln Ile Leu Ser Ile Tyr Ser Thr Val Ala Ser Ser Leu Ala
            515                 520                 525
Leu Ala Ile Met Met Ala Gly Leu Ser Leu Trp Met Cys Ser Ser Gly
            530                 535                 540
Arg Leu Val Pro Arg Gly Ser Pro Gly Ser Gly Tyr Ile Pro Glu Ala
545                 550                 555                 560
Pro Arg Asp Gly Gln Ala Tyr Val Arg Lys Asp Gly Glu Trp Val Leu
                565                 570                 575
Leu Ser Thr Phe Leu Gly His His His His His
            580                 585

<210> SEQ ID NO 2
<211> LENGTH: 1776
<212> TYPE: DNA
<213> ORGANISM: Artificial Sequence
<220> FEATURE:
<223> OTHER INFORMATION: Recombinant H5 haemagglutinin (ECD-TMD-foldon)

<400> SEQUENCE: 2
gatcccgggg atcagatttg cattggttac catgcaaaca attcaacaga gcaggttgac      60
acaatcatgg aaaagaacgt tactgttaca catgcccaag atatactgga aaagacacac     120
aacgggaagc tctgcgatct agatggagtg aagcctctaa ttttaagaga ttgtagtgta     180
gctggatggc tcctcgggaa cccaatgtgt gacgaattca tcaatgtacc ggaatggtct     240
```

```
tacatagtgg agaaggccaa tccaaccaat gacctctgtt acccagggag tttcaacgac    300
tatgaagaac tgaaacacct attgagcaga ataaaccatt ttgagaaaat tcaaatcatc    360
cccaaaagtt cttggtccga tcatgaagcc tcatcaggag tgagctcagc atgtccatac    420
ctgggaagtc cctcctttt tagaaatgtg gtatggctta tcaaaaagaa cagtacatac    480
ccaacaataa agaaaagcta caataatacc aaccaagaag atcttttggt actgtgggga    540
attcaccatc ctaatgatgc ggcagagcag acaaggctat atcaaaaccc aaccaccctat    600 atttccattg ggacatcaac actaaaccag agattggtac caaaaatagc tactagatcc    660
aaagtaaacg gcaaagtgg aaggatggag ttcttctgga caatttaaa acctaatgat    720 gcaatcaact tcgagagtaa tggaaatttc attgctccag aatatgcata caaaattgtc    780
aagaaagggg actcagcaat tatgaaaagt gaattgaat atggtaactg caacaccaag    840
tgtcaaactc caatgggggc gataaactct agtatgccat tccacaacat acaccctctc    900
accatcgggg aatgccccaa atatgtgaaa tcaaacagat tagtccttgc aacagggctc    960
agaaatagcc ctcaaagaga gagcagaaga aaaaagagag gactatttgg agctatagca   1020
ggttttatag agggaggatg gcagggaatg gtagatggtt ggtatgggta ccaccatagc   1080
aatgagcagg ggagtgggta cgctgcagac aaagaatcca ctcaaaaggc aatagatgga   1140
gtcaccaata aggtcaactc aatcattgac aaaatgaaca ctcagtttga ggccgttgga   1200
agggaattta ataacttaga aaggagaata gagaatttaa acaagaagat ggaagacggg   1260
tttctagatg tctggactta taatgccgaa cttctggttc tcatggaaaa tgagagaact   1320
ctagactttc atgactcaaa tgttaagaac ctctacgaca aggtccgact acagcttagg   1380
gataatgcaa aggagctggg taacggttgt tcgagttct atcacaaatg tgataatgaa   1440
tgtatggaaa gtataagaaa cggaacgtac aactatccgc agtattcaga agaagcaaga   1500
ctaaaaagag aggaaataag tgggggtaaaa ttggaatcaa taggaactta ccaaatactg   1560
tcaatttatt caacagtggc gagttcccta gcactggcaa tcatgatggc tggtctatct   1620
ttatggatgt gctccagcgg ccgcttggtc cctcgtggaa gcccaggctc cggctacatc   1680
cccgaggccc cgcgcgacgg ccaggcctac gtgcgcaagg acggcgagtg ggtgctgctg   1740
tccaccttcc tgggacatca tcatcatcat cattga                              1776
```

<210> SEQ ID NO 3
<211> LENGTH: 10
<212> TYPE: PRT
<213> ORGANISM: Influenza Virus

<400> SEQUENCE: 3

Asn Gly Ser Leu Gln Cys Arg Ile Cys Ile
1               5                   10

<210> SEQ ID NO 4
<211> LENGTH: 30
<212> TYPE: DNA
<213> ORGANISM: Influenza Virus

<400> SEQUENCE: 4
aatggatcgt tacaatgcag aatttgcatt                                       30

<210> SEQ ID NO 5
<211> LENGTH: 38
<212> TYPE: PRT
<213> ORGANISM: Influenza Virus -continued

<400> SEQUENCE: 5

Gly Val Lys Leu Glu Ser Ile Gly Thr Tyr Gln Ile Leu Ser Ile Tyr
1               5                   10                  15

Ser Thr Val Ala Ser Ser Leu Ala Leu Ala Ile Met Met Ala Gly Leu
            20                  25                  30

Ser Leu Trp Met Cys Ser
        35

<210> SEQ ID NO 6
<211> LENGTH: 114
<212> TYPE: DNA
<213> ORGANISM: Influenza Virus

<400> SEQUENCE: 6
ggggtaaaat tggaatcaat aggaacttac caaatactgt caatttattc aacagtggcg      60
agttccctag cactggcaat catgatggct ggtctatctt tatggatgtg ctcc          114

<210> SEQ ID NO 7
<211> LENGTH: 504
<212> TYPE: PRT
<213> ORGANISM: Influenza Virus

<400> SEQUENCE: 7

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Thr His Asn Gly Lys Leu Cys Asp Leu Asp Gly Val Lys
        35                  40                  45

Pro Leu Ile Leu Arg Asp Cys Ser Val Ala Gly Trp Leu Leu Gly Asn
    50                  55                  60

Pro Met Cys Asp Glu Phe Ile Asn Val Pro Glu Trp Ser Tyr Ile Val
65                  70                  75                  80

Glu Lys Ala Asn Pro Thr Asn Asp Leu Cys Tyr Pro Gly Ser Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Ser Asp His Glu Ala Ser
        115                 120                 125

Ser Gly Asx Ser Ser Ala Cys Pro Tyr Leu Gly Ser Pro Ser Phe Phe
    130                 135                 140

Arg Asn Val Val Trp Leu Ile Lys Lys Asn Ser Thr Tyr Pro Thr Ile
145                 150                 155                 160

Lys Lys Ser Tyr Asn Asn Thr Asn Gln Glu Asp Leu Leu Val Leu Trp
                165                 170                 175

Gly Ile His His Pro Asn Asp Ala Ala Glu Gln Thr Arg Leu Tyr Gln
            180                 185                 190

Asn Pro Thr Thr Tyr Ile Ser Ile Gly Thr Ser Thr Leu Asn Gln Arg
        195                 200                 205

Leu Val Pro Lys Ile Ala Thr Arg Ser Lys Val Asn Gly Gln Ser Gly
    210                 215                 220

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Ala Ile Met Lys Ser Glu Leu Glu Tyr Gly
            260                 265                 270
Asn Cys Asn Thr Lys Cys Gln Thr Pro Met Gly Ala Ile Asn Ser Ser
        275                 280                 285
Met Pro Phe His Asn Ile His Pro Leu Thr Ile Gly Glu Cys Pro Lys
    290                 295                 300
Tyr Val Lys Ser Asn Arg Leu Val Leu Ala Thr Gly Leu Arg Asn Ser
305                 310                 315                 320
Pro Gln Arg Glu Ser Arg Arg Lys Lys Arg Gly Leu Phe Gly Ala Ile
                325                 330                 335
Ala Gly Phe Ile Glu Gly Gly Trp Gln Gly Met Val Asp Gly Trp Tyr
            340                 345                 350
Gly Tyr His His Ser Asn Glu Gln Gly Ser Gly Tyr Ala Ala Asp Lys
        355                 360                 365
Glu Ser Thr Gln Lys Ala Ile Asp Gly Val Thr Asn Lys Val Asn Ser
    370                 375                 380
Ile Ile Asp Lys Met Asn Thr Gln Phe Glu Ala Val Gly Arg Glu Phe
385                 390                 395                 400
Asn Asn Leu Glu Arg Arg Ile Glu Asn Leu Asn Lys Lys Met Glu Asp
                405                 410                 415
Gly Phe Leu Asp Val Trp Thr Tyr Asn Ala Glu Leu Leu Val Leu Met
            420                 425                 430
Glu Asn Glu Arg Thr Leu Asp Phe His Asp Ser Asn Val Lys Asn Leu
        435                 440                 445
Tyr Asp Lys Val Arg Leu Gln Leu Arg Asp Asn Ala Lys Glu Leu Gly
    450                 455                 460
Asn Gly Cys Phe Glu Phe Tyr His Lys Cys Asp Asn Glu Cys Met Glu
465                 470                 475                 480
Ser Ile Arg Asn Gly Thr Tyr Asn Tyr Pro Gln Tyr Ser Glu Glu Ala
                485                 490                 495
Arg Leu Lys Arg Glu Glu Ile Ser
            500

<210> SEQ ID NO 8
<211> LENGTH: 1521
<212> TYPE: DNA
<213> ORGANISM: Influenza Virus

<400> SEQUENCE: 8
gatcccgggg atcagatttg cattggttac catgcaaaca attcaacaga gcaggttgac      60
acaatcatgg aaaagaacgt tactgttaca catgcccaag acatactgga aaagacacac     120
aacgggaagc tctgcgatct agatggagtg aagcctctaa ttttaagaga ttgtagtgta     180
gctggatggc tcctcgggaa cccaatgtgt gacgaattca tcaatgtacc ggaatggtct     240
tacatagtgg agaaggccaa tccaaccaat gacctctgtt acccagggag tttcaacgac     300
tatgaagaac tgaaacacct attgagcaga ataaaccatt ttgagaaaat tcaaatcatc     360
cccaaaagtt cttggtccga tcatgaagcc tcatcaggag tgagctcagc atgtccatac     420
ctgggaagtc cctccttttt tagaaatgtg gtatggctta tcaaaagaa cagtacatac     480 ccaacaataa agaaaagcta caataatacc aaccaagaag atcttttggt actgtgggga     540 attaccatc ctaatgatgc ggcagagcag acaaggctat atcaaaaccc aaccacctat     600
atttccattg ggacatcaac actaaaccag agattggtac caaaaatagc tactagatcc     660

| | |
|---|---|
| aaagtaaacg ggcaaagtgg aaggatggag ttcttctgga caattttaaa acctaatgat | 720 |
| gcaatcaact tcgagagtaa tggaaatttc attgctccag aatatgcata caaaattgtc | 780 |
| aagaaagggg actcagcaat tatgaaaagt gaattggaat atggtaactg caacaccaag | 840 |
| tgtcaaactc caatggggggc gataaactct agtatgccat tccacaacat acaccctctc | 900 |
| accatcgggg aatgccccaa atatgtgaaa tcaaacagat tagtccttgc aacagggctc | 960 |
| agaaatagcc ctcaaagaga gagcagaaga aaaagagag gactatttgg agctatagca | 1020 |
| ggttttatag agggaggatg gcagggaatg gtagatggtt ggtatgggta ccaccatagc | 1080 |
| aatgagcagg ggagtgggta cgctgcagac aaagaatcca ctcaaaaggc aatagatgga | 1140 |
| gtcaccaata aggtcaactc aatcattgac aaaatgaaca ctcagtttga ggccgttgga | 1200 |
| agggaattta ataacttaga aaggagaata gagaatttaa acaagaagat ggaagacggg | 1260 |
| tttctagatg tctggactta taatgccgaa cttctggttc tcatggaaaa tgagagaact | 1320 |
| ctagactttc atgactcaaa tgttaagaac ctctacgaca aggtccgact acagcttagg | 1380 |
| gataatgcaa aggagctggg taacggttgt ttcgagttct atcacaaatg tgataatgaa | 1440 |
| tgtatggaaa gtataagaaa cggaacgtac aactatccgc agtattcaga gaagcaaga | 1500 |
| ctaaaaagag aggaaataag t | 1521 |

<210> SEQ ID NO 9
<211> LENGTH: 29
<212> TYPE: PRT
<213> ORGANISM: Bacteriophage

<400> SEQUENCE: 9

Gly Ser Gly Tyr Ile Pro Glu Ala Pro Arg Asp Gly Gln Ala Tyr Val
1               5                   10                  15

Arg Lys Asp Gly Glu Trp Val Leu Leu Ser Thr Phe Leu
            20                  25

<210> SEQ ID NO 10
<211> LENGTH: 87
<212> TYPE: DNA
<213> ORGANISM: Bacteriophage

<400> SEQUENCE: 10

| | |
|---|---|
| ggctccggct acatcccccga ggccccgcgc gacggccagg cctacgtgcg caaggacggc | 60 |
| gagtgggtgc tgctgtccac cttcctg | 87 |

<210> SEQ ID NO 11
<211> LENGTH: 564
<212> TYPE: PRT
<213> ORGANISM: Influenza Virus

<400> SEQUENCE: 11

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Thr His Asn Gly Lys Leu Cys Asp Leu Asp Gly Val Lys
        35                  40                  45

Pro Leu Ile Leu Arg Asp Cys Ser Val Ala Gly Trp Leu Leu Gly Asn
    50                  55                  60

Pro Met Cys Asp Glu Phe Ile Asn Val Pro Glu Trp Ser Tyr Ile Val
65                  70                  75                  80

-continued

```
Glu Lys Ala Asn Pro Thr Asn Asp Leu Cys Tyr Pro Gly Ser Phe Asn
             85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Ser Asp His Glu Ala Ser
        115                 120                 125

Ser Gly Asx Ser Ser Ala Cys Pro Tyr Leu Gly Ser Pro Ser Phe Phe
        130                 135                 140

Arg Asn Val Val Trp Leu Ile Lys Lys Asn Ser Thr Tyr Pro Thr Ile
145                 150                 155                 160

Lys Lys Ser Tyr Asn Asn Thr Asn Gln Glu Asp Leu Leu Val Leu Trp
                165                 170                 175

Gly Ile His His Pro Asn Asp Ala Ala Glu Gln Thr Arg Leu Tyr Gln
            180                 185                 190

Asn Pro Thr Thr Tyr Ile Ser Ile Gly Thr Ser Thr Leu Asn Gln Arg
        195                 200                 205

Leu Val Pro Lys Ile Ala Thr Arg Ser Lys Val Asn Gly Gln Ser Gly
        210                 215                 220

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Ala Ile Met Lys Ser Glu Leu Glu Tyr Gly
            260                 265                 270

Asn Cys Asn Thr Lys Cys Gln Thr Pro Met Gly Ala Ile Asn Ser Ser
        275                 280                 285

Met Pro Phe His Asn Ile His Pro Leu Thr Ile Gly Glu Cys Pro Lys
        290                 295                 300

Tyr Val Lys Ser Asn Arg Leu Val Leu Ala Thr Gly Leu Arg Asn Ser
305                 310                 315                 320

Pro Gln Arg Glu Ser Arg Arg Lys Lys Arg Gly Leu Phe Gly Ala Ile
                325                 330                 335

Ala Gly Phe Ile Glu Gly Gly Trp Gln Gly Met Val Asp Gly Trp Tyr
            340                 345                 350

Gly Tyr His His Ser Asn Glu Gln Gly Ser Gly Tyr Ala Ala Asp Lys
        355                 360                 365

Glu Ser Thr Gln Lys Ala Ile Asp Gly Val Thr Asn Lys Val Asn Ser
        370                 375                 380

Ile Ile Asp Lys Met Asn Thr Gln Phe Glu Ala Val Gly Arg Glu Phe
385                 390                 395                 400

Asn Asn Leu Glu Arg Arg Ile Glu Asn Leu Asn Lys Lys Met Glu Asp
                405                 410                 415

Gly Phe Leu Asp Val Trp Thr Tyr Asn Ala Glu Leu Leu Val Leu Met
            420                 425                 430

Glu Asn Glu Arg Thr Leu Asp Phe His Asp Ser Asn Val Lys Asn Leu
        435                 440                 445

Tyr Asp Lys Val Arg Leu Gln Leu Arg Asp Asn Ala Lys Glu Leu Gly
        450                 455                 460

Asn Gly Cys Phe Glu Phe Tyr His Lys Cys Asp Asn Glu Cys Met Glu
465                 470                 475                 480

Ser Ile Arg Asn Gly Thr Tyr Asn Tyr Pro Gln Tyr Ser Glu Glu Ala
                485                 490                 495

Arg Leu Lys Arg Glu Glu Ile Ser Gly Val Lys Leu Glu Ser Ile Gly
```

```
                    500                 505                 510
Thr Tyr Gln Ile Leu Ser Ile Tyr Ser Thr Val Ala Ser Ser Leu Ala
            515                 520                 525

Leu Ala Ile Met Met Ala Gly Leu Ser Thr Trp Met Cys Ser Asn Gly
        530                 535                 540

Ser Leu Gln Cys Arg Ile Cys Ile Leu Val Pro Arg Gly Ser His His
545                 550                 555                 560

His His His His
```

INFLUENZA ANTIGENS

This application is a § 371 of International Application No. PCT/EP2017/054843, filed 2 Mar. 2017, which claims priority of GB Application No. 1603625.3, filed 2 Mar. 2016.

TECHNICAL FIELD

The present invention relates to novel influenza antigens, novel immunogenic or vaccine compositions, as well as to uses of and to methods for producing said antigens and compositions. In particular, the invention relates to recombinant forms of hemagglutinin (HA) and their use in vaccine compositions for the prevention of influenza virus infections.

BACKGROUND OF THE INVENTION

Influenza viruses are one of the most ubiquitous viruses present in the world, affecting both humans and livestock. Influenza results in an economic burden, morbidity and even mortality, which are significant. There are three types of influenza viruses: A, B and C. Influenza virus comprises two predominant surface antigens, the glycoproteins hemagglutinin (HA) and neuraminidase (NA), which appear as spikes at the surface of the particles. It is these surface proteins, particularly HA, that determine the antigenic specificity of the influenza subtypes.

HA is a trimeric protein comprised of an ectodomain of identical subunits each of which contains two polypeptides, HA1 and HA2, linked by a disulphide bond. Each monomer is initially expressed as HA0, and is subsequently cleaved by host proteases into HA1 and HA2 subunits which are linked via a disulfide bond. HA can be functionally divided into two domains, the globular head and the stalk. The globular head is composed of part of HA1 and the stalk structure is composed of portions of HA1 and all of HA2 (Hai et al, J. Virol, 2012 86(10): 5774-5781).

Vaccination plays a critical role in controlling influenza epidemics and pandemics. Many influenza vaccines are made by methods that involve reassortment, adaptation and growth of viruses in chicken eggs. However there are limitations with these existing methods. Not all influenza virus strains grow well in eggs and must be adapted or viral reassortants constructed. The changes in HA during manufacture can lead to strains that differ from the circulating strains and that may offer suboptimal levels of protection. Another drawback is that those with egg allergies may show hypersensitivity to residual egg proteins in egg based vaccines. Furthermore, egg based methods rely on an uninterrupted supply of eggs, which can be susceptible to disruptions in supply such as disease in poultry. There is a need for production of vaccines using methods that do not rely on egg supply and where vaccine protein production is more stringently controlled than in egg based methods.

Recombinant forms of HA (rHA) produced in culture cells have been proposed as an alternative source of antigen for influenza vaccines to that sourced from eggs. However, problems maintaining immunogenicity and a regular quaternary structure of rHA have been encountered using these methods. There is thus still a need for alternative methods of antigen supply for influenza vaccines, that address the existing challenges.

SUMMARY OF THE INVENTION

It was found with previous efforts at producing rHA that large aggregates of the recombinant protein formed that are not acceptable for vaccine production purposes. Additionally, the correct rosette structure, a multimeric form of the basic trimer structure of HA, did not always correctly form. The inventors have made a recombinant hemagglutinin (rHA) antigen which incorporates a heterologous trimerisation domain such as a foldon, as well as a hydrophobic signal such as the transmembrane domain of HA and the extracellular domain (ECD) or an immunogenic portion thereof. The rHA produced by the inventors is capable of forming the correct rosette structure without large aggregates and maintains immunogenicity. These functional properties render the rHA potentially useful for the treatment and/or prevention of influenza infection and/or disease.

Accordingly, in a first aspect of the invention, there is provided a recombinant influenza virus hemagglutinin (HA) antigen comprising the extracellular domain of HA or an immunogenic portion thereof, a hydrophobic signal and a heterologous trimerisation domain.

In a further aspect there is provided a HA antigen as described above wherein the hydrophobic signal is a HA transmembrane domain or an artificial hydrophobic signal.

In a further aspect there is provided a polynucleotide encoding a recombinant hemagglutinin antigen as described above.

In a further aspect there is provided an immunogenic composition comprising a recombinant antigen as defined above and a pharmaceutically-acceptable carrier.

In a further aspect there is provided the immunogenic composition described above for use in medicine In still a further aspect there is provided the immunogenic composition described above for use in the prevention and/or vaccination against influenza disease In still a further aspect there is provided the immunogenic composition described above for use in the prevention and/or vaccination against influenza caused by a different clade than the clade to which the extracellular domain of the HA antigen described above belongs In still a further aspect there is provided a method for producing a recombinant antigen as defined above comprising expressing a polynucleotide described above in a eukaryotic cell, such as a mammalian cell, e.g. a CHO cell, or an insect cell, optionally further comprising purifying/isolating the rHA from the eukaryotic cell In yet a further aspect there is provided a method for prevention and/or vaccination against influenza disease, comprising the administration of an antigen or immunogenic composition as described above to a person in need thereof, such as a person identified as being at risk of being infected with influenza disease

BRIEF DESCRIPTION OF THE FIGURES

Figure 2:
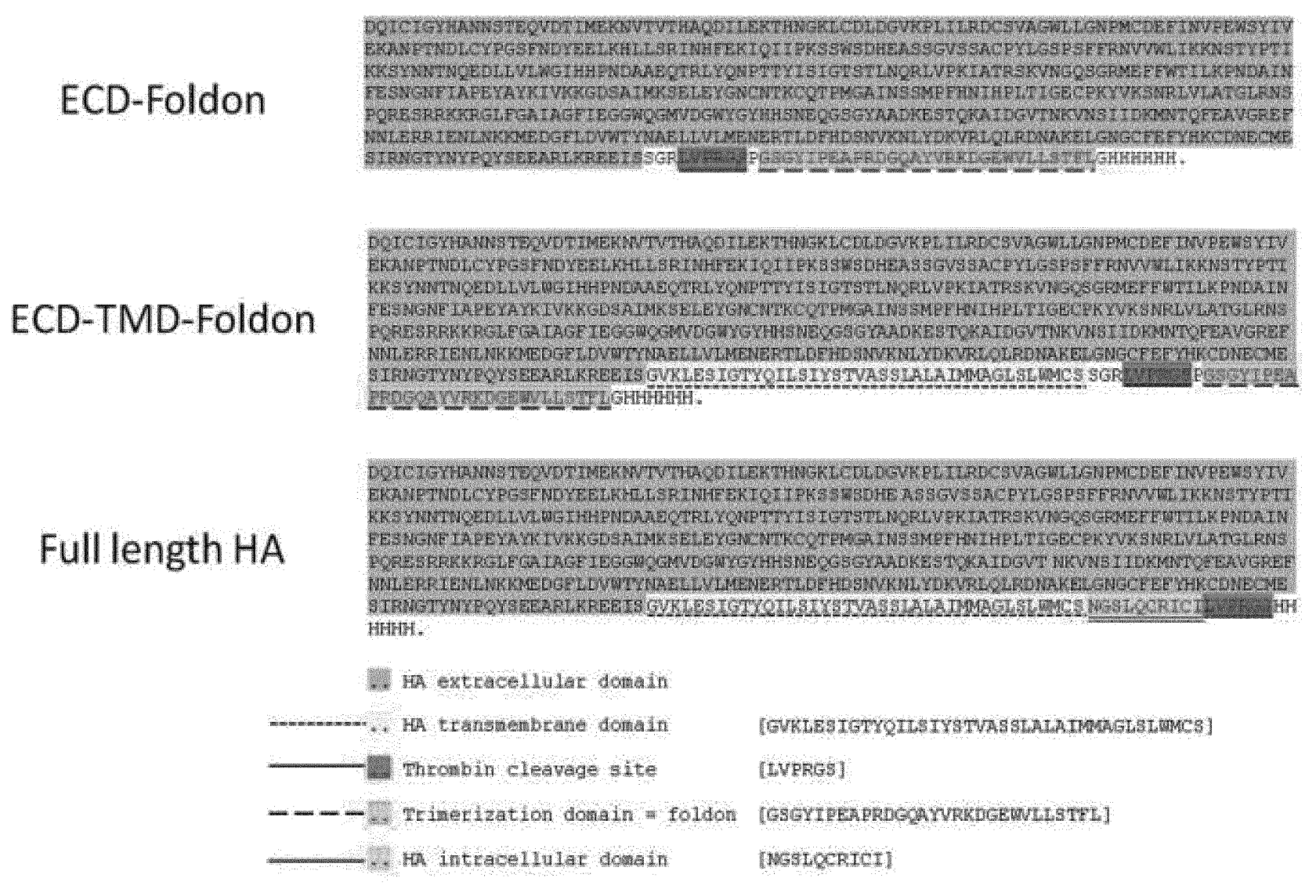

FIG. 2: The amino acid sequences of ECD-Foldon and ECD-TMD-Foldon used in the Examples are shown. A. ECD-Foldon is the starting molecule, and ECD-TMD-Foldon has been designed by inserting the transmembrane domain of HA (TM) between the HA extracellular domain and the Foldon domain of ECD-Foldon. For information, the amino acid sequence of the full-length HA molecule of the same strain that has been used as comparator in this study is also shown.

FIGS. 3A, 3B and 3C: Electron micrographs showing the appearance of ECD-Foldon, ECD-TMD-Foldon and recombinant full-length HA, respectively in solution.

DETAILED DESCRIPTION

Figure 1:
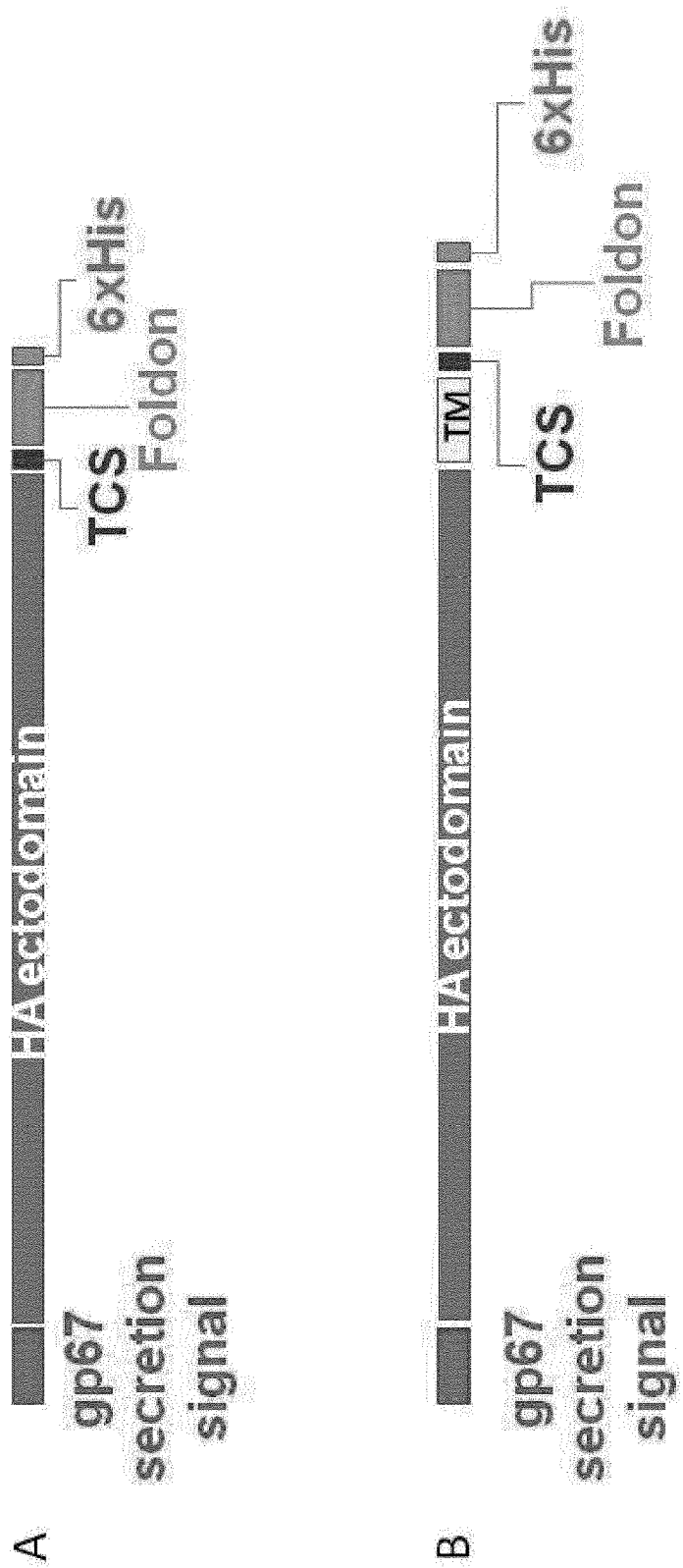
FIG. 1: The design of ECD-Foldon and ECD-TMD-Foldon used in the Examples is shown. A. ECD-Foldon is the starting molecule, composed of the gp67 secretion signal, the ectodomain of HA (ECD), a thrombin cleavage site (TCS), the trimerization domain Foldon and a histidine tail (to facilitate purification). B. ECD-TMD-Foldon has been designed by inserting the transmembrane domain of HA (TM) between the ectodomain and the Foldon domain.

Provided herein is a recombinant influenza virus hemagglutinin (rHA) antigen comprising or consisting of the extracellular domain of HA (ectodomain, ECD) or an immunogenic portion thereof, a hydrophobic signal such as a HA transmembrane domain (TMD) and a heterologous trimerisation domain.

Recombinant Influenza Virus HA (rHA)

A rHA comprises or is encoded by one or more nucleic acids that are derived from a nucleic acid which was artificially constructed. For example, the nucleic acid can comprise, or be encoded by, a cloned nucleic acid formed by joining heterologous nucleic acids.

The rHA includes hemagglutinin-derived sequences (such as the ECD and TMD) and may include other non-hemagglutinin derived sequences, for example a non-hemagglutinin derived heterologous trimerisation domain. Typically, the hemagglutinin-derived sequences are in the order that they appear in naturally derived hemagglutinin and the trimerisation domain occurs towards, or at the C-terminal, for example in the C-terminal half of the rHA/C-terminal to the ECD. The rHA of the invention, may in particular consist or comprise of the ECD of HA or an immunogenic portion thereof followed by a HA TMD, followed by a heterologous trimerisation domain, in that order, wherein the trimerisation domain is in the C-terminal half of the rHA/C-terminal to the ECD.

The rHA antigen of the invention may be fused to or contain further polypeptide other than ECD, TMD and trimerisation domain. The sequence encoding the further polypeptide optionally includes additional features such as a flexible linker between the HA derived sequences and other heterologous amino acid sequences. The linkers can facilitate the independent folding of the HA domains and other heterologous sequences. The linker may be an amino acid sequence that is synthesized as part of a recombinant fusion protein. In other embodiments, a chemical linker is used to connect synthetically or recombinantly produced subsequences. Such flexible linkers are known to those skilled in the art.

In addition to flexible linkers, or alternatively, the fusion proteins optionally include polypeptide subsequences from proteins which are unrelated to hemagglutinin, e.g. a sequence with affinity to a known antibody to facilitate affinity purification and/or detection. Such detection and purification-facilitating domains include, but are not limited to, metal chelating peptides such as polyhistidine tracts and histidine-tryptophan modules that allow purification on immobilized metals and protein A domains that allow purification on immobilized immunoglobulin. Examples include heterologous fusion sequences encoding gD tags, c-Myc epitopes, poly-histidine tags, Fluorescent proteins (e.g. GFP), beta-galactosidase protein or glutathione S transferase or any other sequence useful for detection or purification of the fusion protein expressed in or on a cell. Preferably, the further polypeptide sequence is a polyhistidine tag, such as a six histidine tag. The inclusion of a cleavable linker sequence between the purification domain (e.g. polyhistidine tag) and rHA antigen may be useful to facilitate purification. For example an enzyme cleavage site, such as a thrombin cleavage site may be included between the further polypeptide and the rest of the rHA sequences. A cleavable linker sequence, for example an enzyme cleavage site such as a thrombin cleavage site may alternatively or additionally be included between the trimerisation domain and the rest of the rHA sequences. This can allow the trimerisation domain to be removed in the final rHA. Hence, the rHA antigen of the invention may consist of or comprise (in order) the ECD of HA or an immunogenic portion thereof, a HA TMD, a heterologous trimerisation domain, a purification tag (e.g. polyhistidine tag) and optionally a cleavable linker sequence i) between the purification tag and the rest of the rHA and/or ii) between the trimerisation domain and the HA TMD.

The gene or construct encoding the rHA antigen may include a signal peptide. Typically, the signal peptide is appropriate for the host cell in which the rHA is expressed. In one embodiment, the natural signal peptide sequence in hemagglutinin is deleted and replaced with a baculovirus signal peptide, for example secretion signal gp67 (Whitford et al 1989, J. Virol. 63, 1393-1399), for proper expression in insect cells. The gene containing rHA antigen and baculovirus signal peptide can be introduced into a baculovirus expression vector so that the baculovirus promoter directs the transcription of the fusion proteins in infected insect cells. The signal peptide directs the translation of the rHA antigen into the insect cell glycosylation pathway and is not present on the mature protein.

Accordingly, nucleic acid sequence encoding the rHA antigen of the invention may consist of or comprise sequence encoding the ECD of HA or an immunogenic portion thereof, a HA TMD, a heterologous trimerisation domain (e.g. foldon), a purification tag (e.g. polyhistidine tag) and a signal peptide (e.g. a baculovirus signal peptide), such as in the order: a signal peptide (e.g. a baculovirus signal peptide), the ECD of HA or an immunogenic portion thereof, a HA TMD, a heterologous trimerisation domain (e.g. foldon), a purification tag (e.g. polyhistidine tag). As another example, the nucleic acid encoding the rHA antigen of the invention may consist of or comprise sequence encoding (in order): a signal peptide (e.g. a baculovirus signal peptide), the ECD of HA or an immunogenic portion thereof, a HA TMD, a cleavable linker sequence (e.g. TCS), a heterologous trimerisation domain (e.g. foldon), a purification tag (e.g. polyhistidine tag).

The HA sequences (e.g. the ECD (or immunogenic portion thereof) and TMD) of the rHA antigen may be from any type or subtype (e.g. H1 to H16) of influenza strain. In one embodiment, the HA sequence of the HA antigen is from a strain selected from the group consisting of: an H1, an H2, an H3, an H5, an H7 and an H9 subtype strain. Preferably, the HA antigen is from an H5 strain. The sequences for the ECD (or immunogenic portion thereof) and TMD can be from the same source/strain/type/subtype of influenza.

In some embodiments, the HA has a sequence that is identical to HA from a pandemic strain. By pandemic strain, it is meant a new influenza virus against which the large majority of the human population has no immunity. Typically, the WHO identifies and publicises such pandemic strains. Suitable pandemic strains are, for example H5N1, H9N2, H7N7, H7N9, H2N2, H7N1, H7N3, H10N7, H5N2 and H1N1. Alternatively, the HA sequence is identical or derived from naturally occurring HA from a non-pandemic strain. For example, the non-pandemic strains may be strains identified by WHO as circulating seasonal influenza virus strains or strains identified by WHO as having the potential for causing an epidemic for the subsequent influenza season. Such strains may for example be 1) H1N1, H3N2 influenza A type strains and 2) one or two B type influenza strains (e.g. from Victoria and/or Yamagata lineages).

For example, the rHA antigen of the invention may comprise i) an amino acid sequence comprising the ECD of HA (e.g. SEQ ID NO: 7) or an immunogenic portion or derivative thereof, ii) amino acid sequence comprising an HA TMD (e.g. SEQ ID NO: 5) and iii) the heterologous trimerisation domain (foldon) shown in SEQ ID NO: 9 or a derivative of this sequence that maintains the ability to induce rHA monomers to form trimers. In particular, the ECD of HA may be derived from an H5 virus (e.g. an H5N1 virus), such as that shown in SEQ ID NO: 7. Both the ECD and/or the TMD of HA may be derived from H5 virus such as an H5N1 virus. For example, the rHA antigen may comprise i) SEQ ID NO: 7 or an immunogenic portion or derivative thereof and/or ii) SEQ ID NO: 5 or derivative thereof that retains the ability to orientate the HA trimers into rosette structures and maintains the immunogenicity of HA. In particular, the rHA antigen may comprise or consist of the amino acid sequence shown in SEQ ID NO: 1.

The nucleic acid sequence encoding the rHA antigen may comprise i) nucleic acid encoding the ECD of HA (e.g. SEQ ID NO: 8), or a fragment or derivative of this sequence encoding an immunogenic portion of the HA ECD, ii) nucleic acid sequence (e.g. SEQ ID NO: 6) encoding the TMD of HA or a fragment or derivative of this sequence that encodes a TMD that retains the ability to orientate the HA trimers into rosette structures and maintains the immunogenicity of HA and iii) SEQ ID NO: 10 encoding foldon or a derivative of this sequence that maintains the ability to induce expressed rHA monomers to form trimers.

The ECD and/or TMD sequence may be derived from an H5 virus e.g an H5N1 virus. For example, in one embodiment the nucleic acid sequence encoding the rHA antigen comprises i) SEQ ID NO: 8 or a fragment or derivative of this sequence encoding an immunogenic portion of the HA ECD and ii) SEQ ID NO: 6, or a fragment or derivative of this sequence that encodes a TMD that retains the ability to orientate the HA trimers into rosette structures and maintains the immunogenicity of HA. In particular, nucleic acid encoding the rHA antigen of the invention may consist or comprise of the nucleic acid sequence shown in SEQ ID NO: 2.

In another instance, nucleic acid encoding the rHA antigen of the invention may comprise any nucleic acid sequence encoding an HA ECD, any sequence encoding a HA TMD and the foldon sequence shown in SEQ ID NO: 10 or a derivative of this sequence that maintains the ability to induce expressed rHA monomers to form trimers. In a further instance, nucleic acid encoding the rHA antigen of the invention may comprise i) any nucleic acid sequence encoding an HA ECD, ii) any nucleic acid sequence encoding a heterologous trimerisation domain and iii) SEQ ID NO: 6 encoding the TMD of HA or a fragment or derivative of this sequence that encodes a TMD that retains the ability to orientate the HA trimers into rosette structures and maintains the immunogenicity of HA. In a yet further instance, nucleic acid encoding the rHA of the invention may comprise i) SEQ ID NO: 8 encoding the ECD of HA, or a fragment or derivative of this sequence encoding an immunogenic portion of the HA ECD, ii) any nucleic acid sequence encoding a heterologous trimerisation domain and iii) any nucleic acid encoding a TMD of HA. In a yet further instance still, nucleic acid encoding the rHA antigen of the invention may comprise i) any sequence encoding an ECD of HA, ii) the foldon sequence shown in SEQ ID NO: 10 or a derivative of this sequence that maintains the ability to induce expressed rHA monomers to form trimers and iii) any nucleic acid encoding a TMD of HA.

Preferably, the recombinant influenza virus hemagglutinin (HA) antigen of the invention lacks the intracellular domain of influenza hemagglutinin, e.g. the intracellular domain represented by SEQ ID NO: 3. Also provided is a nucleic acid sequence encoding the recombinant influenza virus hemagglutinin (HA) antigen of the invention that lacks sequence encoding the intracellular domain of influenza hemagglutinin, e.g. the intracellular domain represented by SEQ ID NO:4.

Extracellular Domain (ECD) or Immunogenic Portion Thereof

The extracellular domain (or ectodomain, ECD) component of HA is present in wild-type HA protein at the cell surface. The rHA of the invention may comprise a full length ECD, or an immunogenic portion thereof. The ECD or immunogenic portion thereof, may in some embodiments be a variant or derivative of wild-type HA protein (for example containing amino acid substitutions, deletions or additions).

The immunogenic portion thereof, may include one or more regions of HA for which it is desired to direct an immune response. Such regions may include known conserved and/or variable epitopes of hemagglutinin that elicit neutralising antibodies upon vaccination. Preferably, the portion thereof is capable of proper folding to interact in a hemagluttination assay.

For instance, the ECD may consist or comprise the HA1 and/or HA2 region of HA. Alternatively, the ECD may consist or comprise the head and/or stalk region of HA. An ECD may consist or comprise the HA2 subunit and a portion of the HA1 subunit, that together form the stalk region of HA. The ECD may consist of the stalk region of HA, a so-called "headless" form of HA. In particular, in some embodiments, the HA antigen may lack the HA head, or part of the head, such as more than 25% e.g. more than 50%, such as more than 75% of the amino acid residues of the head, or lack the HA1 part of the head. Alternatively, the HA sequence may lack the HA stalk, or part of the stalk, such as more than 25%, e.g. more than 50%, such as more than 75% of the amino acid residues of the stalk, or lack the HA2 part of the stalk.

The terms "HA1" refers to the region of the HA protein including amino acid residues from approximately 1-330 of the extracellular domain of HA protein. HA1 comprises all residues that are N-terminal to the HA1/HA2 cleavage peptide of the precursor HA0 protein, including the receptor binding domain of the HA protein.

The term "HA2" refers to the region of the HA protein including amino acid residues from approximately 331-504 of the HA0 haemagglutin polypeptide. Of note, these residues within the HA2 chain are commonly numbered independently of those in HA1, such that HA2 residues may be numbered consecutively 1-174. The HA2 chain comprises all residues that are C-terminal to the HA1/HA2 cleavage peptide of the precursor HA0 protein, including the hydrophobic peptide responsible for insertion within the host cell membrane during the process of membrane fusion.

The term "HA stalk" refers to the region of the HA protein including residues from approximately 1-42 and 274-330 of the HA1 chain as well as residues (1-174) of the HA2 chain.

The stalk is located in the membrane-proximal region of the HA, directly beneath the vestigial esterase domain of the HA1 globular head.

The term "HA head" refers to a globular head region of the HA protein excluding the transmembrane domain and any intracellular region, which is composed of part of HA1 and that contains a sialic acid binding pocket that mediates virus attachment to the host cell. See for example Hai et al (J. Virol, 2012 86(10): 5774-5781).

Numbering of the amino acid sequence of the ECD is consecutive from the amino (N—) terminal to the carboxyl (C—) terminal residue, such that position 1 corresponds to the residue at the N-terminus of each sub-domain in the wild type HA as found in virions. As such, any additional engineered residues at the N-terminus, such as the heterologous sequences described herein, and those introduced as part of the expression strategy or for the purposes of solubilisation or purification, are numbered in the reverse order (i.e. from —C) to N-terminal) from position 1, starting with position 0 (e.g. 0, −1, −2, etc).

The ECD sequence may be derived from any type or subtype (e.g. H1 to H16) of influenza strain. In one embodiment, the HA ECD sequence is from a strain selected from the group consisting of: an H1, an H2, an H3, an H5, an H7 and an H9 subtype strain. Preferably, the ECD is from an H5 strain such as an H5N1 strain.

For example, the HA ECD may comprise or consist of the amino acid sequence shown in SEQ ID NO: 7 or a fragment or derivative of this sequence that contains an immunogenic portion of HA. Nucleic acid encoding the HA ECD may comprise or consist of the nucleic acid sequence shown in SEQ ID NO: 8 or a fragment or derivative of this sequence encoding an immunogenic portion of the HA ECD.

The term "hydrophobic signal" refers to a stretch of at least 5 or at least 6 hydrophobic aminoacids, or refers to an overall structure where the hydrophobic aminoacids are surface exposed. Hydrophobic signals may be natural or artificial. Natural hydrophobic signals are present in cellular or viral transmembrane proteins. Any natural or artificial hydrophobic signals must retain the original function in the protein, e.g. in case of HA proteins, the hydrophobic signal must have the ability to orientate the HA trimers into rosette structures. The hydrophobic signal naturally present in HA proteins is named the transmembrane domain.

Transmembrane Domain (TMD)

The transmembrane domain may consist or comprise a full length TMD from a wild-type HA protein or a truncation or derivative thereof. Any truncation or derivative thereof must retain the ability to orientate the HA trimers into rosette structures and maintain the immunogenicity of HA. The proper rosette structure can be detected using techniques well known to those skilled in the art such as electron microscopy.

The transmembrane domain may also be derived from any type or type or subtype (e.g. H1 to H16) of influenza strain. In one embodiment, the HA TMD sequence is from a strain selected from the group consisting of: an H1, an H2, an H3, an H5, an H7 and an H9 strain. Preferably, the TMD is from an H5 strain such as an H5N1 strain. The TMD may be derived from the same or a different strain to the ECD sequences. The TMD may be either homologous or heterologous to the ECD. For example, the HA TMD may comprise or consist of the amino acid sequence shown in SEQ ID NO: 5 or a fragment or derivative of this sequence that retains the ability to orientate HA trimers into rosette structures and maintains the immunogenicity of HA. Nucleic acid encoding the HA TMD may comprise or consist of the nucleic acid sequence shown in SEQ ID NO: 6 or a fragment or derivative of this sequence encoding a TMD that retains the ability to orientate HA trimers into rosette structures and maintains the immunogenicity of HA.

Trimerisation Domain

A suitable trimerisation domain is one that induces rHA monomers to form trimers. Preferably the trimerisation domain is or is derived from the natural trimerisation domain of T4 phage fibritin "foldon". A 29 amino acid foldon sequence may be used which forms a β-propeller structure comprising the C terminus of the fibritin domain of the T4 bacteriophage. Other suitable trimerisation domains include chloramphenicol acetyl transferase (CAT) and a leucine zipper trimerisation motif derived from the yeast transcription activator GCN4. Most preferably, the trimerisation domain, such as foldon, is placed at the C terminus of the HA extracellular domain and TMD (e.g. stem domain). Typically, the trimerisation domain is fused via a short linker region to the HA sequence. The region between the trimerisation domain and HA sequence may include a cleavable linker sequence, so it is possible to isolate the HA sequence from the trimerisation at later stages. Thus, the HA sequence (which includes the ECD and TMD) may be linked (e.g. in order), optionally via a linker sequence, to heterologous sequence comprising a protease cleavage site, the trimerisation domain and a purification tag such as histidine tag to aid in purification. Such heterologous trimerisation domains may be linked to HA sequences by techniques known in the art, such as molecular cloning.

For example, the trimerisation domain may comprise or consist of the foldon amino acid sequence shown in SEQ ID NO: 9 or a derivative of this sequence that maintains the ability to induce rHA monomers to form trimers. Nucleic acid encoding the trimerisation domain may consist of or comprise SEQ ID NO: 10 or a derivative of this sequence that maintains the ability to induce expressed rHA monomers to form trimers, e.g. as evaluated by electron microscopy.

Methods of Preparing rHA

Use of recombinant DNA technology to produce influenza vaccines offers several advantages. This includes avoiding the steps of adaptation and passage of infectious viruses in eggs and production of more highly purified protein under safer and more stringently controlled conditions. Moreover, no virus inactivation step has to be included. Any suitable cloning and expression system may be used to recombinantly produce the rHA antigen.

Nucleotide sequences encoding the rHA antigens of the invention may be synthesized, and/or cloned and expressed according to techniques well known to those in the art. See for example, Sambrook, et al, Molecular Cloning, A Laboratory Manual, Vols. 1-3, Cold Spring Harbor Press, Cold Spring Harbor, N.Y. (1989). In some embodiments, the polynucleotide sequences will be codon optimised for a particular recipient host cell using standard methodologies. For example, a DNA construct encoding a hemagglutinin sequence can be codon optimised for expression in other hosts, e.g. bacteria, mammalian or insect cells. Suitable host cells may include bacterial cells such as *E. Coli*, fungal cells such as yeast, insect cells such as *Drosophila* S2, *Spodoptera* Sf9, Sf00+ or Hi-5 and animal cells such as CHO.

Hemagglutinin sequences may be produced by standard recombinant methods known in the art, such as polymerase chain reaction (PCR) or reverse transcriptase PCR, reverse engineering or the DNA can be synthesized. For PCR, primers can be prepared using hemagglutinin nucleotide sequences that are available in publicly available databases. Polynucleotide constructs may be assembled from PCR cassettes and sequentially cloned into a vector containing a selectable marker for propagation in a host cell.

A recombinant vector can then be introduced into the host cell by injection, transfection or electroporation or other methods (for example, calcium phosphate transfection, DEAE-dextran mediated transfection, cationic lipid-mediated transfection, electroporation). Commercial transfection reagents such as Lipofectamine (Invitrogen, Carlsbad, Calif.) are also available.

The rHA antigen can be recovered and purified from recombinant cell cultures by methods known in the art, including anion and/or cation exchange chromatography, affinity chromatography. Techniques such as SDS-PAGE can be used to analyse fractions of protein eluted from these separation/purification techniques. Such methods are well known to those skilled in the art and will not be presented in detail here.

Proper folding of the rHA antigen can be determined for example by using the red blood cell hemagglutination assay, by the ability of the protein to bind an influenza receptor, by immunogenicity testing in a host animal and/or determination of the ability of the protein to assume an appropriate quaternary structure such as rosette formation.

Preferably a baculovirus expression system is used, which is described below.

Baculovirus Expression System

When using a baculovirus expression system, the rHA antigen of interest together with any heterologous sequence (for example HA sequences together with the trimerisation domain) can be inserted into a baculovirus expression vector. Recombinant baculovirus that express foreign genes can be made by homologous recombination between baculovirus DNA and plasmids containing the insert, using well known techniques. The insertion may, for example be made so that the insert is under the transcription control of the polyhedron promoter, the baculovirus promoter.

Example of baculovirus expression vectors including a vector derived from the well characterised *Autographa californica* Nuclear Polyhedrosis Virus (AcNPV) which replicates efficiently in susceptible cultured insect cells.

Any suitable insect host cell can be used to produce the recombinant HA antigen, including but not limited to Sf900+, Sf9 or Hi-5 cells. Preferably, the insect host cell is Sf9 or Hi-5. Cells may be propagated with culture medium and culture conditions known to be suitable for the selected host cell. Cells may be propagated for example in monolayer or in free suspension culture.

rHA protein may then be isolated from the host cells using methods well known in the art. For example, the cell culture may be centrifuged, the supernatant collected and run through appropriate anionic and/or cationic exchange columns to purify the protein. Techniques such as SDS-PAGE and/or immunoblotting may be used to check the identity and integrity of proteins. A fraction of interest containing rHA may then be further purified, for example by passing through a nickel column so that rHA displaying a histidine tag binds the nickel in the column.

The extent of trimerisation and/or multimerisation (e.g. rosette formation) may be tested for example by crosslinking of HA using a suitable crosslinking agent and then use of gel migration techniques, as well known in the art. Other techniques include electron microscopy or spectroscopy based techniques that are also well known to those skilled in the art.

Rosette Formation

In one embodiment, the rHA antigen of the present invention is found in the form of rosettes. The rosettes consist of multimers of the HA trimers having a rosette-like structure. The rosettes are visible for example in an electron microscope. More quantitative techniques can also be used to measure rosette formation, including gel filtration and spectroscopy based techniques. Rosettes generally comprise 20-100 HA trimers/particle. The particle size of the rosette structures range from 20-40 nanometers (nm) in length. HA sediments as a rosette comprised of 5-6 trimers over the pH range 7.4-7.5 (Remeta et al 2002, Biochem. 41, 2044-2054). It is thought that the hydrophilic C-terminal portions of HA trimers concentrate together into a core region from which the hydrophobic regions splay out like a snowflake or rosette structure.

Immunogenic Composition

In a further aspect, an immunogenic composition comprising an HA antigen of the invention and a pharmaceutically acceptable carrier is provided.

In one embodiment, said composition further comprises an adjuvant. Preferably, the adjuvant is an oil-in-water emulsion adjuvant. Oil in water emulsion adjuvants, such as MF59 or AS03 are well known in the art and are described below.

In one embodiment, the composition is monovalent, i.e. only comprises one influenza HA. In alternative embodiments, the composition is multivalent, i.e. comprises multiple influenza virus antigens. For example, the composition may be bivalent, trivalent or quadrivalent, e.g. may contain two or three seasonal strains with the rHA of the invention.

Adjuvant

In one embodiment, an immunogenic composition of the invention comprises an adjuvant. In particular, the adjuvant may be an emulsion, such as an oil-in-water emulsion. Optionally, other immunostimulants may be present in the oil-in-water emulsion. In a specific embodiment, an oil-in-water emulsion comprises a metabolisable oil, non-toxic oil such as squalene or squalane, optionally a tocol such as tocopherol in particular alpha tocopherol and an emulsifier (or surfactant) such as the non-ionic surfactant polyoxyethylene sorbitan monooleate (TWEEN-80 ™ or polysorbate 80™). Mixtures of surfactants can be used such as polyoxyethylene sorbitan monooleate/sorbitan trioleate (SPAN 85™) mixtures, or polyoxyethylene sorbitan monooleate/t-octylphenoxypolyethoxyethanol (TRITON X-100™) mixtures.

Tocols (e.g. Vitamin E) are also used in oil emulsions adjuvants (EP0382271B1; U.S. Pat. No. 5,667,784; WO95/17210). Tocols used in oil emulsions (optionally oil-in-water emulsions) may be formulated as described in U.S. Pat. Nos. 5,650,155A; 5,667,784A; EP0382271B1, in that the tocols may be dispersions of tocol droplets, optionally comprising an emulsifier, of optionally less than 1 micron in diameter. Alternatively, the tocols may be used in combination with another oil, to form the oil phase of an oil emulsion. Examples of oil emulsions which may be used in combination with the tocol are described herein, such as the metabolisable oils described above. In an oil-in-water emulsion, the oil and emulsifier should be in an aqueous carrier. The aqueous carrier may be, for example, phosphate buffered saline or a citrate buffer. One example of a tocol-containing oil-in-water emulsion is AS03.

A preferred oil-in-water emulsion comprises a metabolisable oil, such as squalene, Tween 80 and optionally alpha tocopherol. Additionally, the oil-in-water emulsion may contain Span 85™ and/or lecithin.

In one aspect, the oil-in-water emulsion has one of the following compositions:
  From 0.5 to 11 mg squalene, from 0.05 to 5% polyoxyethylene sorbitan monooleate (TWEEN-80 ™ or POLYSORBATE 80™) and optionally, from 2 to 12% alpha-tocopherol; or
  About 5% squalene, about 0.5% polyoxyethylene sorbitan monooleate (TWEEN-80 ™ or POLYSORBATE 80™) and about 0.5% sorbitan trioleate (SPAN 85™). This adjuvant is called MF59.

An alternative adjuvant that may be used with the compositions, vaccine or antigen according the present invention, comprises an immunologically active saponin fraction derived from the bark of Quillaja Saponaria Molina (e.g. QS21) presented in the form of a liposome and a lipopolysaccharide (e.g. 3D-MPL), optionally further including a sterol (cholesterol). In one embodiment, the adjuvant comprises or consists of a saponin (e.g. QS21) presented in the form of a liposome, a lipid A derivative such as 3D-MPL and a sterol (e.g. cholesterol). The liposomes suitably contain a neutral lipid, for example, phosphatidylcholine, dioleoyl phosphatidylcholine (DOPC) or dilauryl phosphatidylcholine. The liposomes may also contain a charged lipid which increases the stability of the liposome-QS21 structure for liposomes composed of saturated lipids. An example of such an adjuvant is AS01, which comprises 3D-MPL and QS21 in a quenched form with cholesterol, and can be made as described in WO96/33739. Either the AS01B or AS01E forms of this adjuvant may be used. The AS01 B adjuvant comprises liposomes, which in turn comprise dioleoyl phosphatidylcholine (DOPC), cholesterol and 3D-MPL (in an amount of approximately 1000 micrograms DOPC, 250 micrograms cholesterol and 50 micrograms 3D-MPL per vaccine dose), QS21 (50 micrograms/dose), phosphate NaCl buffer and water to a volume of 0.5 ml.

The AS01E adjuvant comprises the same ingredients than AS01 B but at a lower concentration in an amount of approximately 500 micrograms DOPC, 125 micrograms cholesterol, 25 micrograms 3D-MPL and 25 micrograms QS21, phosphate NaCl buffer and water to a volume of 0.5 ml.

Vaccination Regimes, Dosing and Efficacy Criteria

Suitably, the immunogenic compositions for use according to the present invention are a standard 0.5 ml injectable dose in most cases, and contain 15 µg or less, of hemagglutinin antigen component from an influenza virus strain, as measured by single radial immunodiffusion (SRD) (J. M. Wood et al.: J. M m Biol. Stand. 5 (1977) 237-247; J. M. Wood et al., J. Biol. Stand. 9 (1981) 317-330). Suitably the vaccine dose volume will be from 0.25 ml to 1 ml, in particular a standard 0.5 ml, or 0.7 ml vaccine dose volume. Slight adaptation of the dose volume will be made routinely depending on the HA concentration in the original bulk sample and depending also on the delivery route with smaller doses being given by the intranasal or intradermal route. Suitably said immunogenic compositions for use according to the invention contain a low amount of HA antigen—e.g. any of 1, 2, 3, 4, 5, 6, 7, 8, 9, 10, 11, 12, 13, 14 µg of HA per influenza virus strain or which does not exceed 15 µg of HA per strain. Said low amount of HA amount may be as low as practically feasible provided that it allows to formulate a vaccine which meets the international e.g. EU or FDA criteria for efficacy, as detailed below (see Table 1 and the specific parameters as set forth). A suitable low amount of HA is from 1 to 7.5 µg of HA per influenza virus strain, suitably from 3.5 to 5 µg, such as 3.75 or 3.8 µg of HA per influenza virus strain, typically about 5 µg of HA per influenza virus strain. Another suitable amount of HA is from 0.1 to 5 µg of HA per influenza virus strain, suitably from 1.0 to 2 µg of HA per influenza virus strain, such as 1.9 µg of HA per influenza virus strain.

The influenza medicament (e.g. immunogenic composition) of the invention suitably meets certain international criteria for vaccines. Standards are applied internationally to measure the efficacy of influenza vaccines.

Serological variables are assessed according to criteria of the European Agency for the Evaluation of Medicinal Products for human use (CHMP/BWP/214/96, Committee for Proprietary Medicinal Products (CPMP). Note for harmonization of requirements for influenza vaccines, 1997. CHMP/BWP/214/96 circular No 96-0666:1-22) for clinical trials related to annual licensing procedures of influenza vaccines (Table below).

TABLE 1

| CHMP criteria | | |
| --- | --- | --- |
| | 18-60 years | >60 years |
| Seroconversion rate* | >40% | >30% |
| Conversion factor** | >2.5 | >2.0 |
| Protection rate*** | >70% | >60% |

*Seroconversion rate is defined as the proportion of subjects in each group having a protective post-vaccination titre ≥ 1:40. The seroconversion rate simply put is the % of subjects who have an HI titre before vaccination of <1:10 and ≥1:40 after vaccination. However, if the initial titre is ≥1:10 then there needs to be at least a fourfold increase in the amount of antibody after vaccination.
**Conversion factor is defined as the fold increase in serum HI geometric mean titres (GMTs) after vaccination, for each vaccine strain.
***Protection rate is defined as the proportion of subjects who were either seronegative prior to vaccination and have a (protective) post-vaccination HI titre of ≥1:40 or who were seropositive prior to vaccination and have a significant 4-fold increase in titre post-vaccination; it is normally accepted as indicating protection.

The requirements are different for adult populations (18-60 years) and elderly populations (>60 years). For interpandemic influenza vaccines, at least one of the assessments (seroconversion factor, seroconversion rate, seroprotection rate) should meet the European requirements, for all strains of influenza included in the vaccine. The proportion of titres equal or greater than 1:40 is regarded most relevant because these titres are expected to be the best correlate of protection (Beyer et al. (1998) Clin Drug Invest 15:1).

The compositions for use according to the present invention suitably meet at least one such criteria for the influenza virus strain included in the composition (one criteria is enough to obtain approval), suitably at least two, or typically at least all three criteria for protection. Suitably the above response(s) is(are) obtained after one dose, or after two doses.

Methods of Treatment

In a further embodiment, the HA antigen or immunogenic composition comprising said antigen is for use in medicine, such as for use in the prevention of, or vaccination against, influenza e.g. administered to a person (e.g. subject) at risk for influenza infection.

In a yet further embodiment, the HA antigen or immunogenic composition comprising said antigen is for use in the prevention of influenza caused by a different clade than the clade on which the HA antigen was based. For example, a H5N1 clade 1 HA antigen could be used for protection against influenza caused by a non-clade 1 virus e.g. a H5N1 clade 2 virus.

In a further aspect, there is provided a method of prevention and/or treatment against influenza disease, comprising the administration of an antigen or immunogenic composition as described herein to a person in need thereof, e.g. to a person (e.g. subject) at risk for influenza infection, e.g. an elderly person (age 50 or over, particularly age 65 or over).

In one embodiment of the above described method or use, less than 15 micrgrams, such as from 3.75 to 10 micrograms of HA is administered per dose.

In one aspect, the invention provides the rHA of the invention at a dose of below 10 micrograms, or below 8 micrograms, or from 1-7.5 micrograms, or from 1-5 micrograms of rHA for use in a vaccination regimen for the prevention of influenza, wherein the hemagglutinin sequences are from, or derived from a strain of influenza identified by an international organisation such as the WHO that monitors outbreaks of influenza virus, as associated with a pandemic outbreak or as having the potential to be associated with a future pandemic outbreak.

Routes of Administration

The composition of the invention may be administered by any suitable delivery route, such as intradermal, mucosal (e.g. intranasal), oral, intramuscular or subcutaneous. Other delivery routes are well known in the art.

The intramuscular delivery route is particularly suitable for the adjuvanted influenza composition. The composition according to the invention may be presented in a monodose container, or alternatively, a multidose container, particularly suitable for a pandemic vaccine. In this instance an antimicrobial preservative such a thiomersal may be present to prevent contamination during use. A thiomersal concentration of 5 µg/0.5 ml dose (i.e. 10 µg/ml) or 10 µg/0.5 ml dose (i.e. 20 µg/ml) is suitably present. A suitable IM delivery device could be used such as a needle-free liquid jet injection device, for example the Biojector 2000 (Bioject, Portland, Oreg.). Alternatively a pen-injector device, such as is used for at-home delivery of epinephrine, could be used to allow self administration of vaccine. The use of such delivery devices may be particularly amenable to large scale immunization campaigns such as would be required during a pandemic.

Intradermal delivery is another suitable route. Any suitable device may be used for intradermal delivery, for example short needle devices. Such devices are well known in the art. Intradermal vaccines may also be administered by devices which limit the effective penetration length of a needle into the skin, such as those described in WO99/34850 and EP1092444, incorporated herein by reference, and functional equivalents thereof. Also suitable are jet injection devices which deliver liquid vaccines to the dermis via a liquid jet injector or via a needle which pierces the stratum corneum and produces a jet which reaches the dermis. Also suitable, are ballistic powder/particle delivery devices which use compressed gas to accelerate vaccine in powder form through the outer layers of the skin to the dermis. Additionally, conventional syringes may be used in the classical mantoux method of intradermal administration.

Another suitable administration route is the subcutaneous route. Any suitable device may be used for subcutaneous delivery, for example classical needle. Suitably, a needle-free jet injector service is used. Such devices are well known in the art. Suitably said device is pre-filled with the liquid vaccine formulation.

Alternatively the vaccine is administered intranasally. Typically, the vaccine is administered locally to the nasopharyngeal area, suitably without being inhaled into the lungs. It is desirable to use an intranasal delivery device which delivers the vaccine formulation to the nasopharyngeal area, without or substantially without it entering the lungs.

Suitable devices for intranasal administration of the vaccines according to the invention are spray devices. Suitable commercially available nasal spray devices include Accuspray™ (Becton Dickinson). Nebulisers produce a very fine spray which can be easily inhaled into the lungs and therefore does not efficiently reach the nasal mucosa. Nebulisers are therefore not preferred. Suitable spray devices for intranasal use are devices for which the performance of the device is not dependent upon the pressure applied by the user. These devices are known as pressure threshold devices. Liquid is released from the nozzle only when a threshold pressure is applied. These devices make it easier to achieve a spray with a regular droplet size. Pressure threshold devices suitable for use with the present invention are known in the art and are described for example in WO 91/13281 and EP 311 863 B and EP 516 636, incorporated herein by reference. Such devices are commercially available from Pfeiffer GmbH and are also described in Bommer, R. Pharmaceutical Technology Europe, September 1999.

Alternatively, the epidermal or transdermal vaccination route is also contemplated in the present invention.

The teaching of all references in the present application, including patent applications and granted patents, are herein fully incorporated by reference. Any patent application to which this application claims priority is incorporated by reference herein in its entirety in the manner described herein for publications and references.

For the avoidance of doubt the terms 'comprising', 'comprise' and 'comprises' herein is intended by the inventors to be optionally substitutable with the terms 'consisting of', 'consist of', and 'consists of', respectively, in every instance.

The invention will be further described by reference to the following, non-limiting, examples:

EXAMPLES

Example 1: Design and Construction of ECD-TMD-Foldon Hemagglutinin Antigen (HA) Plasmid Hemagglutinin (HA) antigen was modified based on a native HA protein of A/Indonesia/05/2005 H5N1 strain. At the N-terminus, the HA signal peptide was replaced by gp67, which is a very effective baculovirus-encoded signal sequence for protein secretion (Whitford et al 1989, J. Virol. 63, 1393-1399). Transmembrane domain (TMD), needed for the rosette formation, as well as trimerization domain Foldon (from bacteriophage T4 fibritin) (Meier et al 2004, J. Mol. Biol. 344, 1051-1069), needed for the trimerization of HA monomers, were downstream the HA sequence (ECD). Finally, a poly-His tag was added at the C-terminus to facilitate the purification of the recombinant antigen.

FIG. 1 shows the composition of the starting construct ECD-Foldon and that of ECD-TMD-Foldon. ECD-Foldon was a gift from the Center for Diseases Control (CDC, Atlanta, USA). This construct was incorporated in plasmid pAcGP67, a baculovirus transfer vector containing the gp67 signal sequence in front of ECD-Foldon. ECD-Foldon was used as template to prepare the other construct and was first produced by transformation of electrocompetent TOP10 *Escherichia coli* cells (Life Technologies). The plasmid DNA of ECD-Foldon was purified by Maxiprep (Qiagen), according to the manufacturer's instructions. It was used to construct ECD-TMD-Foldon by inserting the TM between ECD and Foldon by site-directed mutagenesis. For that, a megaprimer was first generated by PCR. The primers consisted of sequences complementary to the pAcGP67 vector together with TM sequences, and the template was HA full length from A/Indonesia/05/2005 strain in TOPO plasmid. After PCR reaction, the megaprimer was purified in agarose gel with a QIAquick gel extraction kit (Qiagen). Consecutive mutagenesis reaction was made in the following conditions: 7.5 μl 10×reaction buffer, 2 μl dNTP (10 mM), 100 ng template DNA containing ECD-Foldon; 150 ng Megaprimer, 2 μl PfuUltra HF DNA pol (2.5 U/μl), for a total volume of 50 μl. The PCR conditions were 95° C. for 1 min and then 5 cycles consisting of 50 s at 95° C., 1 min at 52° C., 22 min at 68° C., followed by 13 cycles consisting of 50 s at 95° C., 1 min at 55° C., and 22 min at 68° C. Thereafter, DNA template was removed by Dpn I digestion (Promega). PCR product was used to transform TOP10 electrocompetent cells. Miniprep purification procedure was made on positive colonies and the validity of the construction was confirmed by sequencing. FIG. 2 discloses the full amino acid sequences of ECD-Foldon and ECD-TMD-Foldon. The sequence of the recombinant full-length HA molecule that has been used as comparator, particularly in immunogenicity studies is also shown.

Example 2: Production and Purification of ECD-TMD-Foldon

The construct was inserted in baculovirus. For that, Hi-5 cells in SF-900 II medium containing 264 g/l NaCl were seeded in a 6-well plate at a concentration of $1\times10^6$ cells/well. Fifty ng of the transfer plasmid containing ECD-TMD-Foldon sequence were mixed with 20 ng of BAC vector 3000 and 100 μl Cellfectin reagent (Life technology; cat 10362-010) in SF-900 II medium and incubated during 30 min. Then, 800 μl of medium were added to the transfection mixture and the solution was distributed among the wells. After 5 h incubation, the mixture was removed and replaced with 2 ml of medium. Incubation occurred at 27° C. for 4 days.

Cells and medium were harvested from the 6-well plates, transferred in centrifuge tubes and centrifuged to separate cells from virus-containing medium. Supernatant was used to infect Hi-5 cells. Positive clones were selected based on recombinant protein expression (as checked by Western blotting) and used to generate virus stock.

To purify ECD-TMD-Foldon, a total of 5-10 litres of a suspension of Hi-5 cells (adjusted at $2\times10^6$ cells/ml in SF500 shake flasks) was infected with ECD-TMD-Foldon-modified baculovirus with a multiplicity of infection=1. Harvest occurred 56-65 h after infection. The suspension was centrifuged at 200×g for 30 min and the supernatant discarded. Then 200-250 ml of buffer containing 1% Triton X100 was added to each pellet for a 30 min incubation at 4° C. on a shaking plate to resuspend the pellet. Suspension was centrifuged at 10 000×g for 25 min and the supernatant containing ECD-TMD-Foldon was kept. Recombinant ECD-TMD-Foldon was purified from the supernatant by ion exchange chromatography through an anion exchange column (Q sepharose Fast Flow, Amersham) followed by a cation exchange column (SP sepharose Fast Flow, Amersham). Recombinant molecule bound in SP column was eluted by pH change (5.9 to 7.2) and molarity change (+150 mM NaCl). Sodium dodecyl sulphate polyacrylamide gel electrophoresis (SDS-PAGE) was used to identify the fractions of interest containing the target recombinant molecule. Finally, a pool of the selected interesting fractions was run through a nickel column to further purify ECD-TMD-Foldon that displays a poly-His tag able to bind nickel. Equilibration buffer was 50 mM Tris, pH 8.0-150 mM NaCl and 10 mM imidazole. Fractions were eluted with increasing concentrations of imidazole. Fractions of interest were selected after run in SDS-PAGE. Imidazole was eliminated by dialysis and the sample concentration was adjusted to 1 mg/ml.

Example 3: Characterisation (Including Rosette Formation) of ECD-TMD-Foldon

After purification, full-length HA, ECD-Foldon and ECD-TMD-Foldon were compared by electron microscopy (EM). The samples were prepared for EM negative staining analysis according to a standard two-step negative staining method using phosphotungstic acid as contrasting agent. A glow discharge was applied on the grids to improve the adsorption of the material on the grids. Briefly, a nickel grid (400-mesh) with carbon-coated formvar film was floated on a drop of the sample for 10 min at room temperature to allow adsorption of the material. Excess solution was removed. The grid was briefly floated on a drop of distilled water to remove salt excess and was then transferred on a drop of stain prepared as follows: 2% (w/v) Na phosphotungstate in water supplemented with 1% trehalose (w/v). The grid was blotted dry after 30 s. The material was left to dry completely and examined by transmission electron microscopy under a LEO Zeiss EM912Ω at 100 kV.

Figure 3C:
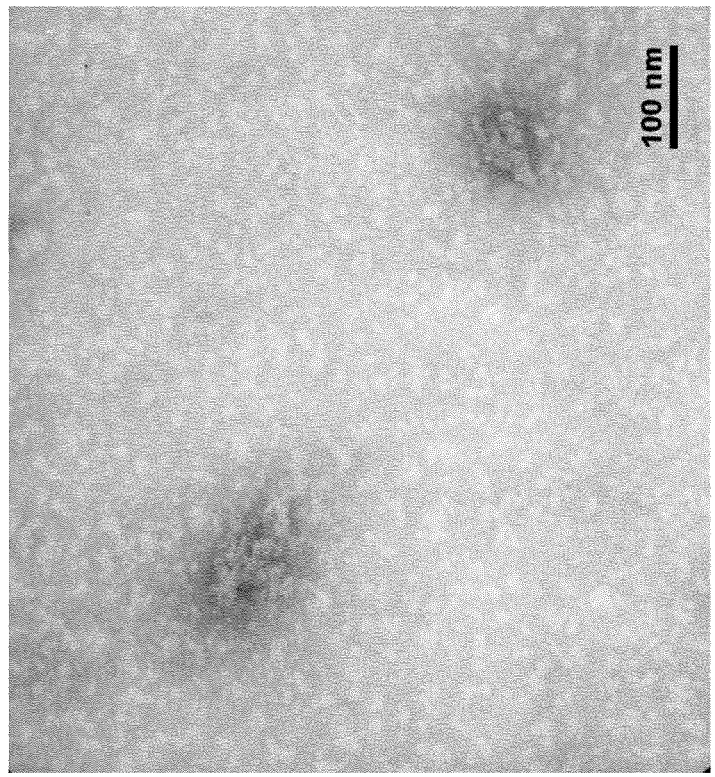
Figure 4:
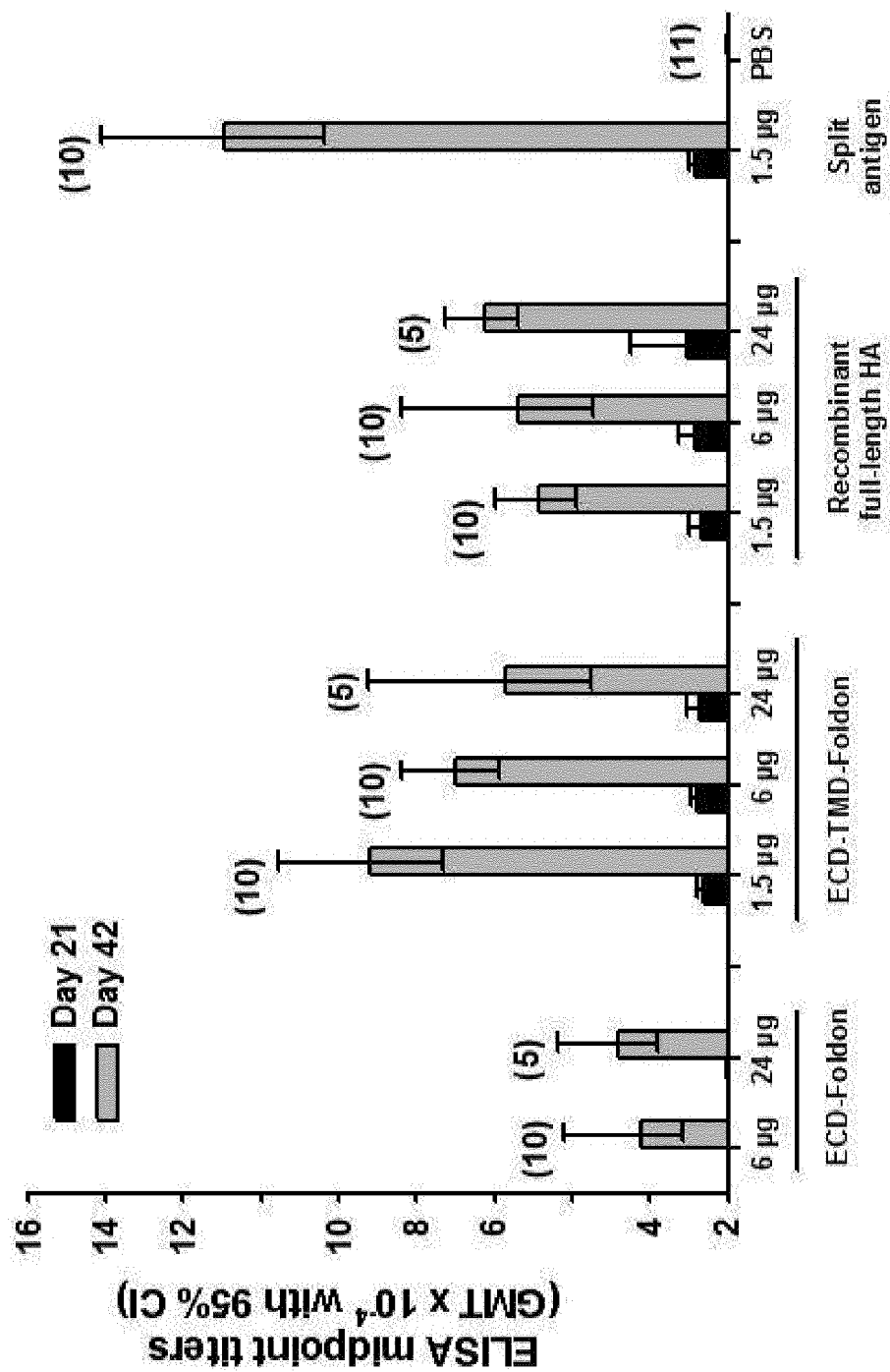
FIG. 4: Mice were immunized on Days 0 and 21 with ECD-Foldon (6 or 24 µg), ECD-TMD-Foldon (1.5, 6 or 24 µg), a recombinant full-length HA antigen (1.5, 6 or 24 µg), split A/Indonesia/05/2005 (1.5 µg), or PBS. Blood was taken on Days 21 and 42 (3 weeks post immunizations) and levels of anti-A/Indonesia/05/2005 antibodies were measured in mouse sera by ELISA. Number in brackets indicate the number of mice in the group.
Figure 5:
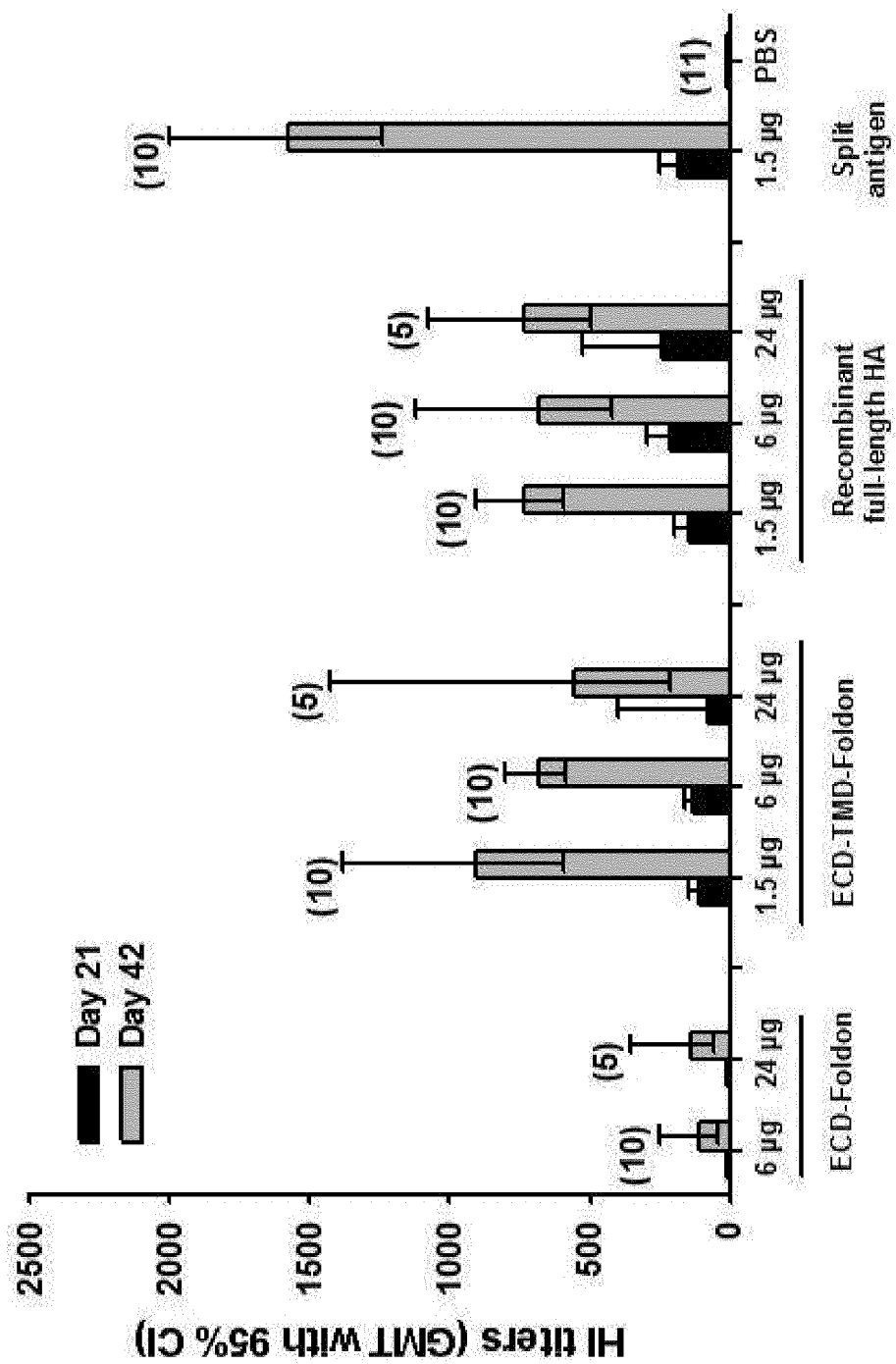
FIG. 5: Mice were immunized on Days 0 and 21 with ECD-Foldon (6 or 24 µg), ECD-TMD-Foldon (1.5, 6 or 24 µg), a recombinant full-length HA antigen (1.5, 6 or 24 µg), split A/Indonesia/05/2005 (1.5 µg), or PBS. Blood was taken on Days 21 and 42 (3 weeks post immunizations) and levels of anti-A/Indonesia/05/2005 antibodies were measured in mouse sera by hemagglutination inhibition assay (HI). Numbers in brackets indicate the number of mice in the group.
Figure 6:
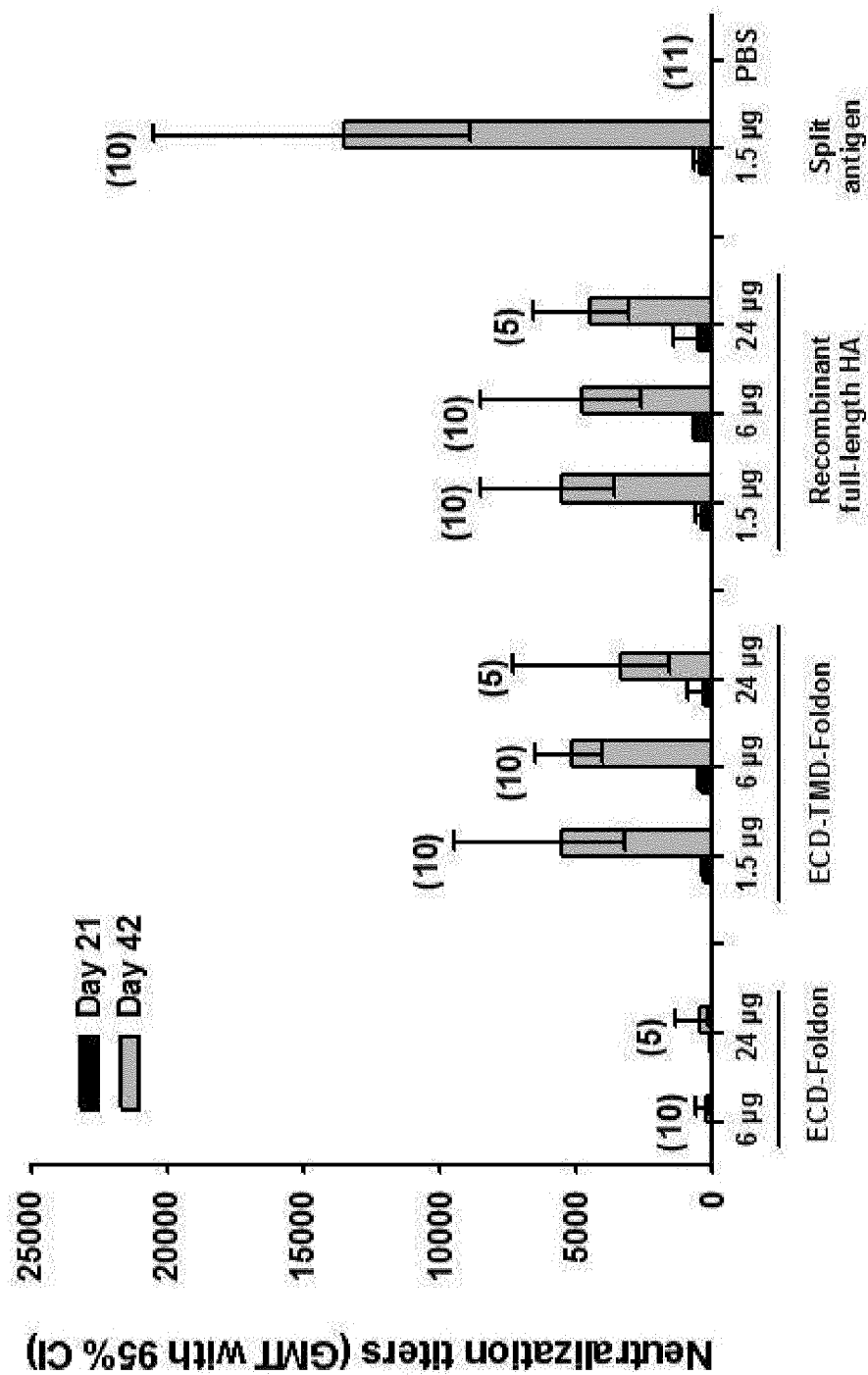
FIG. 6: Mice were immunized on Days 0 and 21 with ECD-Foldon (6 or 24 µg), ECD-TMD-Foldon (1.5, 6 or 24 µg), a recombinant full-length HA antigen (1.5, 6 or 24 µg), split A/Indonesia/05/2005 (1.5 µg), or PBS. Blood was taken on Days 21 and 42 (3 weeks post immunizations) and levels of anti-A/Indonesia/05/2005 neutralizing antibodies were measured in mouse sera by neutralization assay. Numbers in brackets indicate the number of mice in the group.
Figure 7:
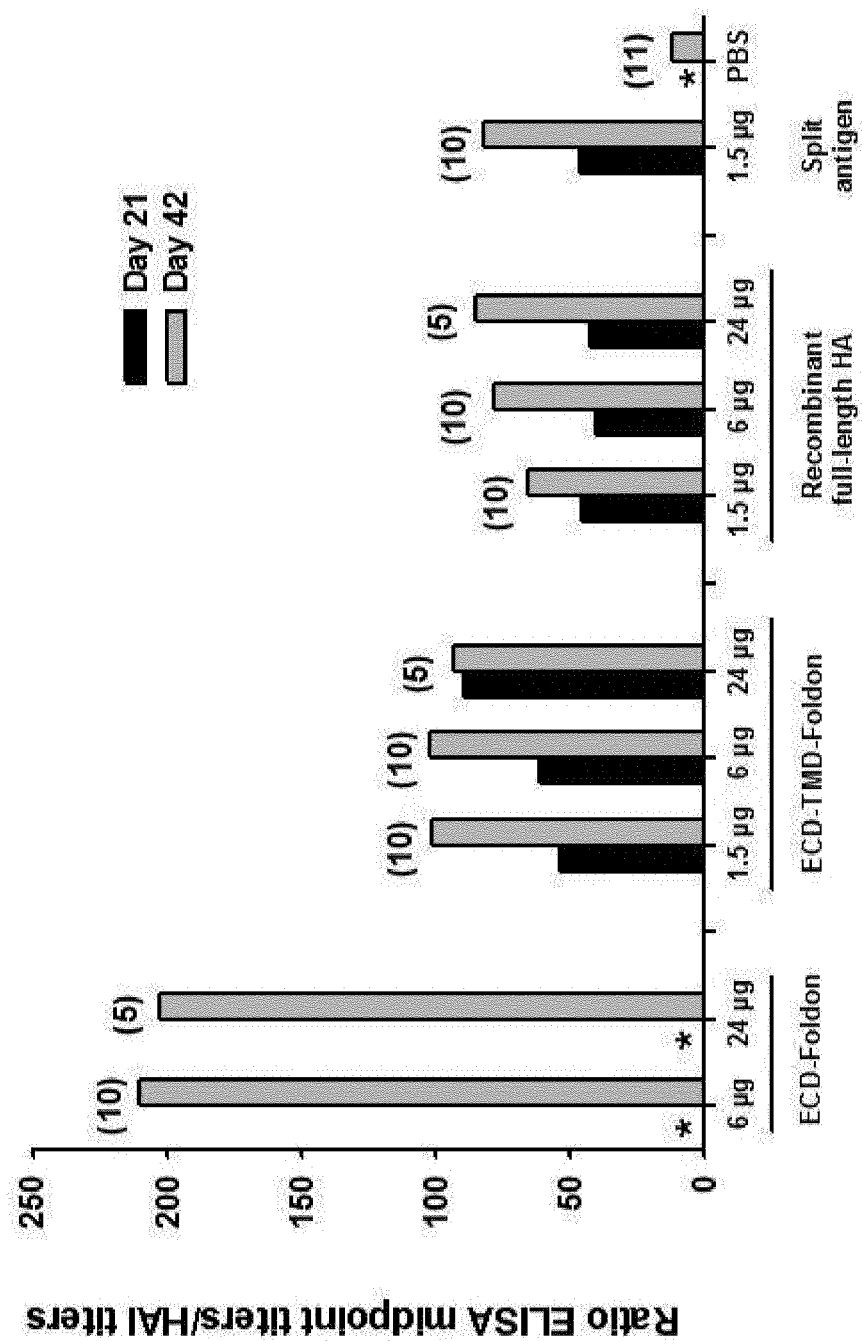
FIG. 7: Mice were immunized on Days 0 and 21 with ECD-Foldon (6 or 24 µg), ECD-TMD-Foldon (1.5, 6 or 24 µg), a recombinant full-length HA antigen (1.5, 6 or 24 µg), split A/Indonesia/05/2005 (1.5 µg), or PBS. Blood was taken on Days 21 and 42 (3 weeks post immunizations) and levels of anti-A/Indonesia/05/2005 antibodies were measured in mouse sera by ELISA and hemagglutination assay. Graph shows the ratios between ELISA and HI values. Numbers in brackets indicate the number of mice in the group. Asterisk (*) indicates that ratio could not be calculated as at least one of the two values was below the cut-off of the assay.
Figure 8:
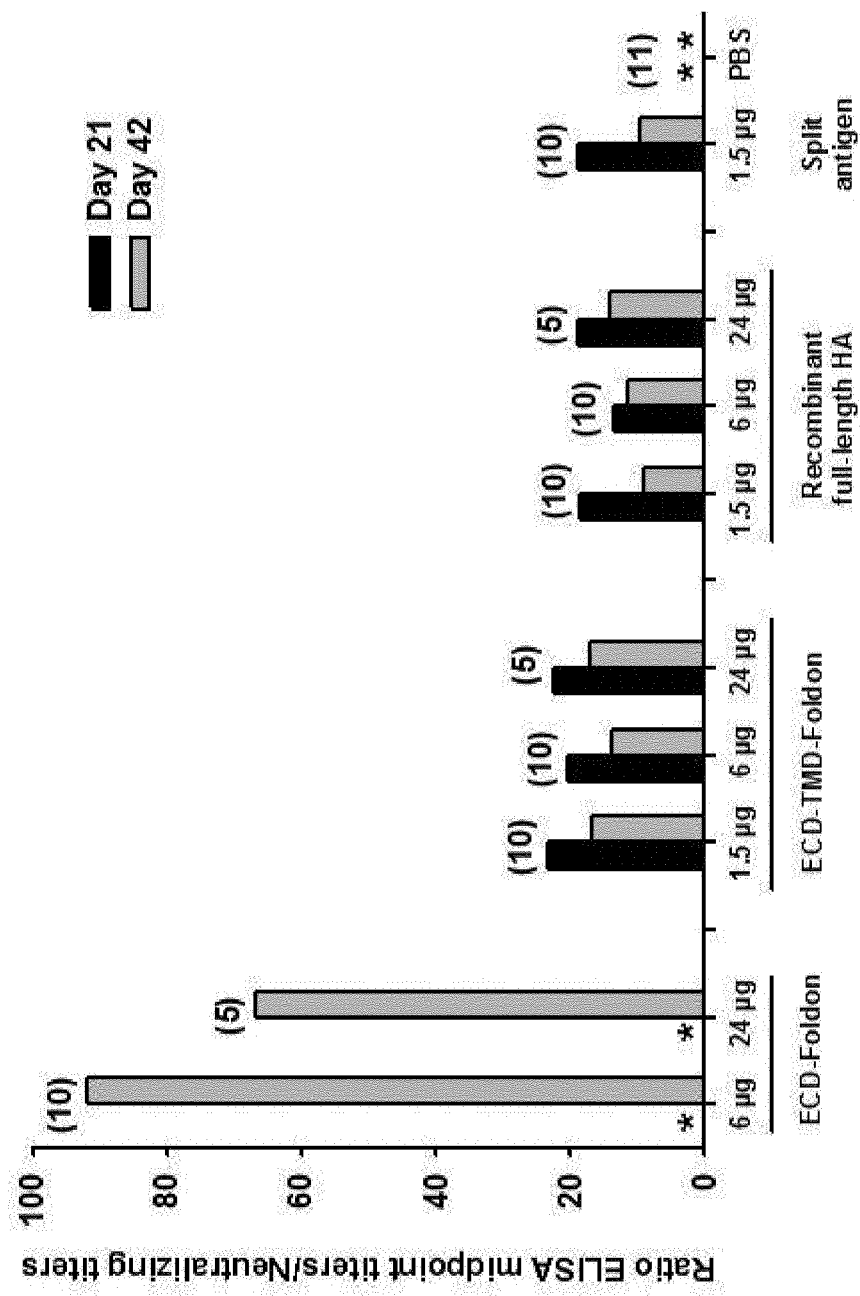
FIG. 8: Mice were immunized on Days 0 and 21 with ECD-Foldon (6 or 24 µg), ECD-TMD-Foldon (1.5, 6 or 24 µg), a recombinant full-length HA antigen (1.5, 6 or 24 µg), split A/Indonesia/05/2005 (1.5 µg), or PBS. Blood was taken on Days 21 and 42 (3 weeks post immunizations) and levels of anti-A/Indonesia/05/2005 antibodies were measured in mouse sera by ELISA and levels of neutraliziong antibodies by neutralization assay. Graph shows the ratios between ELISA and neutralizing values. Number in brackets indicate the number of mice in the group. Asterisk (*) indicates that ratio could not be calculated as at least one of the two values was below the cut-off of the assay.

The results are shown in FIGS. 3A, 3B and 3C. ECD-Foldon appeared as structures of approximately 10 nm. In contrast, both full-length HA and ECD-TMS-Foldon microphotographs showed components ranging from 10 to 50 nm. This indicates that ECD-TMD-Foldon may assemble as a trimeric structure and can form rosette, similarly to full-length HA.

Example 4: ECD-TMD-Foldon is Immunogenic and Elicits Neutralising Antibodies The major drawback of the ECD-Foldon construct was its very poor immunogenicity, compared with split HA antigen. One of the critical factor for immunogenicity of recombinant HA antigens is the possibility to oligomerize and form rosettes. Rosette formation results from the interaction of several HA molecules through their transmembrane domain. Therefore, the transmembrane domain has been inserted in ECD-Foldon with the aim of allowing the formation of rosette and increase immunogenicity, resulting in the ECD-TMD-Foldon construct.

To evaluate immunogenicity of the different constructs female C57Bl/6 mice (8-10-week old; 5, 10 or 11 mice/group)) were immunized at Day 0 and Day 21 with ECD-Foldon (6 or 24 μg), ECD-TMD-Foldon (1.5, 6 or 24 μg), recombinant full-length HA (1.5, 6 or 24 μg), A/Indonesia/05/2005 split antigen (1.5 μg) or phosphate-buffered saline (PBS) negative control. All antigens were adjuvanted with AS03, an Adjuvant System containing α-tocopherol and squalene in an oil-in-water emulsion (Garcon et al 2012, Expert. Rev. Vaccines 11, 349-366). Blood was taken on Days 21 (3 weeks after dose I) and 42 (3 weeks after dose II).

Anti-A/Indonesia/05/2005 antibodies were determined by enzyme-linked immunosorbent assay (ELISA). For that, microtiter plates were coated overnight with A/Indonesia/05/2005 split antigen (1 μg/ml in Dulbecco's phosphate-buffered saline [DPBS]) at 4° C. After saturation of the aspecific sites by a saturation buffer (without serum), serial two-fold dilutions of the mouse sera were added to the wells and incubated for 1.5 h at 37° C. Dilutions were done in the saturation buffer. After wells were washed with PBS-Tween 0.1%, peroxidase-conjugated anti-mouse IgG antibody (Sigma, A5278) was added and incubated for 1 h at 37° C. Bound antibodies were revealed by the addition of the peroxidase substrate orthophenylenediamine in the presence of hydrogen peroxide for 20 min at room temperature in the dark. The colorimetric reaction was stopped by addition of sulphuric acid 2 N and plates were read in a microtiter plate reader. Results are shown in FIG. 4. It was observed that ECD-TMD-Foldon is more immunogenic than ECD-Foldon, but it does not elicit as high levels of antibodies as the corresponding split antigen.

The humoral immune responses were also evaluated by measurement of haemagglutination-inhibition antibody (HI) titers. The day before the assay, 50 μl of receptor destroying enzyme (RDE; cholera filtrate; Sigma C-8772), diluted at 25% in DPBS, was added to 12.5 μl of mouse serum sample and the mixture was incubated 18 h at 37° C. Then, 37.5 μl of sodium citrate 2.5% was added to the mixture and incubated 30 min at 56° C., and DPBS was added for a total volume of 125 μl. After centrifugation, supernatant was diluted 1/10th and serial twofold dilutions of it were pipetted in a microtiterplate. To each well was added 25 μl of a virus suspension (4 UHA in DPBS) for an incubation of 30 min at room temperature. Finally, 50 μl of equine erythrocytes (1% in DPBS) was added and incubated for 1.5-2 h at room temperature. Results are shown in FIG. 5. All ECD-TMD-Foldon, recombinant full-length HA and split antigen groups were different from the two ECD-Foldon groups and not different from each other 3 weeks after the second immunization (One-Way ANOVA followed by Tuckey-HSD post-test).

The functionality of the immunization-induced antibodies was assessed by in vitro flu neutralization assay. For that, mouse serum sample was serially diluted twofold and dilutions were dropped in a microtiter plate (100 μl/well). To the samples, 50 μl of viral solution (2000 $TCID_{50}$/ml) was added and the mixture was incubated for 1.5 h at room temperature. After incubation, 100 μl of Madin-Darby canine kidney (MDCK) cell suspension ($2.4\times10^5$ cells/ml cell culture medium) was added per well. The microtiter plate was placed in an incubator (35° C. with 5% $CO_2$) for 5-7 days. After incubation, 50 μl of the supernatants in each well were transferred in another microtiter plate. To each well, 50 μl of chicken erythrocytes (0.5% in PBS) were added and incubated for 1 h at room temperature. Results are shown in FIG. 6. All ECD-TMD-Foldon, recombinant full-length HA and split antigen groups were different from the two ECD-Foldon groups and not different from each other 3 weeks after the second immunization (One-Way ANOVA followed by Tuckey-HSD post-test).

FIGS. 7 & 8 show the HI and neutralizing activities, respectively, relatively to the levels of antibodies. The ratios for ECD-TMS-Foldon are in the same range as the ratios obtained for the split antigen.

Sequence Listing

```
SEQ ID NO: 1: Amino acid sequence of recombinant H5 hemagglutinin (ECD-TMD-foldon) Indo05
DQICIGYHANNSTEQVDTIMEKNVTVTHAQDILEKTHNGKLCDLDGVKPLILRDCSVAGWLLGNPMCDEFINVP
EWSYIVEKANPTNDLCYPGSFNDYEELKHLLSRINHFEKIQIIPKSSWSDHEASSGBSSACPYLGSPSFFRNVVWL
IKKNSTYPTIKKSYNNTNQEDLLVLWGIHHPNDAAEQTRLYQNPTTYISIGTSTLNQRLVPKIATRSKVNGQSGR
MEFFWTILKPNDAINFESNGNFIAPEYAYKIVKKGDSAIMKSELEYGNCNTKCQTPMGAINSSPMFHNIHPLTIGE
CPKYBKSNRLVLATGLRNSPQRESRRKKRGLFGAIAGFIEGGWQGMVDGWYGYHHSNEQGSGYAADKESTQK
AIDGVTNIWNSIIDKMNTQFEAVGREFNNLERRIENLNKKMEDGFLDVWTYNAELLVLMENERTLDFHDSNVKN
LYDKVRLQLRDNAKELGNGCFEFYHKCDNECMESIRNGTYNYPQYSEEARLKREEISGVKLESIGTYQILSIYSTV
ASSLALAIMMAGLSLWMCSSGRLVPRGSPGSGYIPEAPRDGQAYVRKDGEWVLLSTFLGHHHHHH SEQ ID NO: 2 nucleic acid sequence of recombinant H5 hemagglutinin (ECD-TMD-foldon)
GATCCCGGGGATCAGATTTGCATTGGTTACCATGCAAACAATTCAACAGAGCAGGTTGACACAATCATGGAA
AAGAACGTTACTGTTACACATGCCCAAGACATACTGGAAAAGACACACAACGGGAAGCTCTGCGATCTAGAT
```

```
GGAGTGAAGCCTCTAATTTTAAGAGATTGTAGTGTAGCTGGATGGCTCCTCGGGAACCCAATGTGTGACGAA
TTCATCAATGTACCGGAATGGTCTTACATAGTGGAGAAGGCCAATCCAACCAATGACCTCTGTTACCCAGGG
AGTTTCAACGACTATGAAGAACTGAAACACCTATTGAGCAGAATAAACCATTTTGAGAAAATTCAAATCATCC
CCAAAAGTTCTTGGTCCGATCATGAAGCCTCATCAGGAGTGAGCTCAGCATGTCCATACCTGGGAAGTCCCT
CCTTTTTTAGAAATGTGGTATGGCTTATCAAAAGAACAGTACATACCCAACAATAAAGAAAAGCTACAATAA
TACCAACCAAGAAGATCTTTTGGTACTGTGGGGAATTCACCATCCTAATGATGCGGCAGAGCAGACAAGGCT
ATATCAAAACCCAACCACCTATATTTCCATTGGGACATCAACACTAAACCAGAGATTGGTACCAAAAATAGCT
ACTAGATCCAAAGTAAACGGGCAAAGTGGAAGGATGGAGTTCTTCTGGACAATTTTAAAACCTAATGATGCA
ATCAACTTCGAGAGTAATGGAAATTTCATTGCTCCAGAATATGCATACAAAATTGTCAAGAAGGGGACTCAG
CAATTATGAAAAGTGAATTGGAATATGGTAACTGCAACACCAAGTGTCAAACTCCAATGGGGGCGATAAACT
CTAGTATGCCATTCCACAACATACACCCTCTCACCATCGGGGAATGCCCCAAATATGTGAAATCAAACAGATT
AGTCCTTGCAACAGGGCTCAGAAATAGCCCTCAAAGAGAGAGCAGAAGAAAAAAGAGAGGACTATTTGGAGC
TATAGCAGGTTTTATAGAGGGAGGATGGCAGGGAATGGTAGATGGTTGGTATGGGTACCACCATAGCAATG
AGCAGGGGAGTGGGTACGCTGCAGACAAAGAATCCACTCAAAAGGCAATAGATGGAGTCACCAATAAGGTCA
ACTCAATCATTGACAAAATGAACACTCAGTTTGAGGCCGTTGGAAGGGAATTTAATAACTTAGAAAGGAGAA
TAGAGAATTTAAACAAGAAGATGGAAGACGGGTTTCTAGATGTCTGGACTTATAATGCCGAACTTCTGGTTC
TCATGGAAAATGAGAGAACTCTAGACTTTCATGACTCAAATGTTAAGAACCTCTACGACAAGGTCCGACTACA
GCTTAGGGATAATGCAAAGGAGCTGGGTAACGGTTGTTTCGAGTTCTATCACAAATGTGATAATGAATGTAT
GGAAAGTATAAGAAACGGAACGTACAACTATCCGCAGTATTCAGAAGAAGCAAGACTAAAAGAGAGGAAAT
AAGTGGGGTAAAATTGGAATCAATAGGAACTTACCAAATACTGTCAATTTATTCAACAGTGGCGAGTTCCCTA
GCACTGGCAATCATGATGGCTGGTCTATCTTTATGGATGTGCTCCAGCGGCCGCTTGGTCCCTCGTGGAAGC
CCAGGCTCCGGCTACATCCCCGAGGCCCCGCGCGACGGCCAGGCCTACGTGCGCAAGGACGGCGAGTGGGT
GCTGCTGTCCACCTTCCTGGGACATCATCATCATCATCATTGA

SEQ ID NO: 3 amino acid sequence of the intracellular domain of H5 hemagglutinin
NGSLQCRICI SEQ ID NO: 4 nucleic acid sequence of the intracellular domain of H5 hemagglutinin
AATGGATCGTTACAATGCAGAATTTGCATT SEQ ID NO: 5 amino acid sequence of the transmembrane domain of H5 HA
GVKLESIGTYQILSIYSTVASSLALAIMMAGLSLWMCS SEQ ID NO: 6 nucleic acid sequence of the transmembrane domain of H5 HA
GGGGTAAAATTGGAATCAATAGGAACTTACCAAATACTGTCAATTTATTCAACAGTGGCGAGTTCCCTAGCAC
TGGCAATCATGATGGCTGGTCTATCTTTATGGATGTGCTCC SEQ ID NO: 7 amino acid sequence of extracellular domain of H5 HA
DQICIGYHANNSTEQVDTIMEKNVTVTHAQDILEKTHNGKLCDLDGVKPLILRDCSVAGWLLGNPMCDEFINVP
EWSYIVEKANPTNDLCYPGSFNDYEELKHLLSRINHFEKIQIIPKSSWSDHEASSGBSSACPYLGSPSFFRNVVWL
IKKNSTYPTIKKSYNNTNQEDLLVLWGIHHPNDAAEQTRLYQNPTIYISIGTSTLNQRLVPKIATRSKVNGQSGR
MEFFWTILKPNDAINFESNGNFIAPEYAYKIVKKGDSAIMKSELEYGNCNTKCQTPMGAINSSMPFHNIHPLTIGE
CPKYVKSNRLVLATGLRNSPQRESRRKKRGLFGAIAGFIEGGWQGMVDGWYGYHHSNEQGSGYAADKESTQK
AIDGVTNKVNSIIDKMNTQFEAVGREFNNLERRIENLNKKMEDGFLDVWTYNAELLVLMENERTLDFHDSNVKN
LYDKVRLQLRDNAKELGNGCFEFYHKCDNECMESIRNGTYNYPQYSEEARLKREEIS SEQ ID NO: 8 nucleic acid sequence of extracellular domain of H5 HA
GATCCCGGGGATCAGATTTGCATTGGTTACCATGCAAACAATTCAACAGAGCAGGTTGACACAATCATGAA
AAGAACGTTACTGTTACACATGCCCAAGACATACTGGAAAAGAACACACAACGGGAAGCTCTGCGATCTAGAT
GGAGTGAAGCCTCTAATTTTAAGAGATTGTAGTGTAGCTGGATGGCTCCTCGGGAACCCAATGTGTGACGAA
TTCATCAATGTACCGGAATGGTCTTACATAGTGGAGAAGGCCAATCCAACCAATGACCTCTGTTACCCAGGG
AGTTTCAACGACTATGAAGAACTGAAACACCTATTGAGCAGAATAAACCATTTTGAGAAAATTCAAATCATCC
CCAAAAGTTCTTGGTCCGATCATGAAGCCTCATCAGGAGTGAGCTCAGCATGTCCATACCTGGGAAGTCCCT
CCTTTTTTAGAAATGTGGTATGGCTTATCAAAAGAACAGTACATACCCAACAATAAAGAAAAGCTACAATAA
TACCAACCAAGAAGATCTTTTGGTACTGTGGGGAATTCACCATCCTAATGATGCGGCAGAGCAGACAAGGCT
ATATCAAAACCCAACCACCTATATTTCCATTGGGACATCAACACTAAACCAGAGATTGGTACCAAAAATAGCT
ACTAGATCCAAAGTAAACGGGCAAAGTGGAAGGATGGAGTTCTTCTGGACAATTTTAAAACCTAATGATGCA
ATCAACTTCGAGAGTAATGGAAATTTCATTGCTCCAGAATATGCATACAAAATTGTCAAGAAGGGGACTCAG
CAATTATGAAAAGTGAATTGGAATATGGTAACTGCAACACCAAGTGTCAAACTCCAATGGGGGCGATAAACT
CTAGTATGCCATTCCACAACATACACCCTCTCACCATCGGGGAATGCCCCAAATATGTGAAATCAAACAGATT
AGTCCTTGCAACAGGGCTCAGAAATAGCCCTCAAAGAGAGAGCAGAAGAAAAAAGAGAGGACTATTTGGAGC
TATAGCAGGTTTTATAGAGGGAGGATGGCAGGGAATGGTAGATGGTTGGTATGGGTACCACCATAGCAATG
AGCAGGGGAGTGGGTACGCTGCAGACAAAGAATCCACTCAAAAGGCAATAGATGGAGTCACCAATAAGGTCA
ACTCAATCATTGACAAAATGAACACTCAGTTTGAGGCCGTTGGAAGGGAATTTAATAACTTAGAAAGGAGAA
TAGAGAATTTAAACAAGAAGATGGAAGACGGGTTTCTAGATGTCTGGACTTATAATGCCGAACTTCTGGTTC
TCATGGAAAATGAGAGAACTCTAGACTTTCATGACTCAAATGTTAAGAACCTCTACGACAAGGTCCGACTACA
GCTTAGGGATAATGCAAAGGAGCTGGGTAACGGTTGTTTCGAGTTCTATCACAAATGTGATAATGAATGTAT
GGAAAGTATAAGAAACGGAACGTACAACTATCCGCAGTATTCAGAAGAAGCAAGACTAAAAGAGAGGAAAT
AAGT SEQ ID NO: 9 amino acid sequence of T4 bacteriophage fibritin "foldon"
GSGYIPEAPRDGQAYVRKDGEWVLLSTFL SEQ ID NO: 10 nucleic acid sequence of T4 bacteriophage fibritin "foldon"
GGCTCCGGCTACATCCCCGAGGCCCCGCGCGACGGCCAGGCCTACGTGCGCAAGGACGGCGAGTGGGT
GCTGCTGTCCACCTTCCTG
```

Sequence Listing

SEQ ID NO: 11 amino acid sequence of full length HA
DQICIGYHANNSTEQVDTIMEKNVTVTHAQDILEKTHNGKLCDLDGVKPLILRDCSVAGWLLGNPMCDEFI
NVPEWSYIVEKANPTNDLCYPGSFNDYEELKHLLSRINHFEKIQIIPKSSWSDHEASSGBSSACPYLGSPSFF
RNVVWLIKKNSTYPTIKKSYNNTNQEDLLVLWGIHHPNDAAEQTRLYQNPTTYISIGTSTLNQRLVPKIATR
SKVNGQSGRMEFFWTILKPNDAINFESNGNFIAPEYAYKIVKKGDSAIMKSELEYGNCNTKCQTPMGAINS
SMPFHNIHPLTIGECPKYVKSNRLVLATGLRNSPQRESRRKKRGLFGAIAGFIEGGWQGMVDGWYGYHHS
NEQGSGYAADKESTQKAIDGVTNKVNSIIDKMNTQFEAVGREFNNLERRIENLNKKMEDGFLDVWTYNAE
LLVLMENERTLDFHDSNVKNLYDKVRLQLRDNAKELGNGCFEFYHKCDNECMESIRNGTYNYPQYSEEARL
KREEISGVKLESIGTYQILSIYSTVASSLALAIMMAGLSTWMCSNGSLQCRICILVPRGSHHHHHH

The invention claimed is:

1. A recombinant influenza virus hemagglutinin (HA) antigen comprising the extracellular domain of HA (HA ECD), followed by a hydrophobic signal, followed by a heterologous trimerisation domain, wherein the hydrophobic signal comprises a stretch of at least 5 hydrophobic amino acids.

2. The HA antigen of claim 1, wherein said hydrophobic signal is a HA transmembrane domain (HA TMD).

3. The HA antigen of claim 1, wherein the HA antigen lacks the intracellular domain of influenza hemagglutinin.

4. The HA antigen of claim 1, wherein the hemagglutinin is not full length hemagglutinin.

5. The HA antigen of claim 1, wherein the HA antigen forms rosette structures in vivo.

6. The HA antigen of claim 1, wherein the HA antigen forms rosette structures in vitro.

7. The HA antigen of claim 1 which additionally comprises a His tag.

8. The HA antigen of claim 1 which additionally comprises a cleavable linkage.

9. The HA antigen of claim 1, wherein the hemagglutinin is from an H1, H2, H3, H5, H7 or H9 strain.

10. The HA antigen of claim 2, wherein the HA TMD is heterologous to the extracellular domain of said HA.

11. The HA antigen of claim 1, wherein the hemagglutinin is from an H5 strain.

12. The HA antigen of claim 2, wherein i) the HA ECD consists of or comprises SEQ ID NO: 7, ii) the hydrophobic signal consists of or comprises the HA TMD of SEQ ID NO: 5 or a fragment or derivative of this sequence that retains the ability to orientate HA trimers into rosette structures and maintains the immunogenicity of HA and/or iii) the trimerisation domain consists of or comprises SEQ ID NO: 9 or a derivative of this sequence that maintains the ability to induce rHA monomers to form trimers.

13. The HA antigen of claim 12, wherein i) the HA ECD consists of or comprises SEQ ID NO: 7, ii) the HA TMD consists of or comprises SEQ ID NO:5 and iii) the trimerisation domain consists of or comprises SEQ ID NO: 9.

14. The HA antigen of claim 1, wherein the HA antigen comprises the sequence of SEQ ID NO:1.

15. The HA antigen of claim 1, wherein the hemagglutinin lacks the HA stalk, or part of the stalk.

16. A polynucleotide encoding the HA antigen as described in claim 1.

17. The polynucleotide of claim 16 which comprises i) SEQ ID NO: 8, ii) SEQ ID NO: 6 or a fragment or derivative of this sequence that encodes a TMD that retains the ability to orientate the HA trimers into rosette structures and maintains the immunogenicity of HA and iii) SEQ ID NO: 10 or a derivative of this sequence that maintains the ability to induce expressed rHA monomers to form trimers.

18. The polynucleotide of claim 17 which comprises i) SEQ ID NO:8, ii) SEQ ID NO: 6 and iii) SEQ ID NO:10.

19. The polynucleotide of claim 16 which comprises SEQ ID NO:2.

20. An immunogenic composition comprising the HA antigen as defined in claim 1 and a pharmaceutically-acceptable carrier.

21. The immunogenic composition according to claim 20, further comprising an adjuvant.

22. The immunogenic composition according to claim 21, wherein the adjuvant is an oil-in-water emulsion adjuvant.

23. The immunogenic composition according to claim 20, wherein the composition is multivalent.

24. The immunogenic composition according to claim 20, wherein the composition is monovalent.

25. The HA antigen of claim 6, wherein the rosette structures range in size from 10 to 50 nm.

26. The HA antigen of claim 1, wherein the hydrophobic amino acids are surface exposed.

* * * * *